US010612048B2

(12) United States Patent
Foody et al.

(10) Patent No.: US 10,612,048 B2
(45) Date of Patent: Apr. 7, 2020

(54) METHOD FOR REDUCING WATER USAGE IN A CELLULOSIC CONVERSION PROCESS

(75) Inventors: Patrick J. Foody, Ottawa (CA); Ziyad Rahme, Ottawa (CA)

(73) Assignee: Iogen Energy Corporation, Ottawa (CA)

(*) Notice: Subject to any disclaimer, the term of this patent is extended or adjusted under 35 U.S.C. 154(b) by 164 days.

(21) Appl. No.: 14/123,331

(22) PCT Filed: Jun. 28, 2012

(86) PCT No.: PCT/CA2012/050438
§ 371 (c)(1),
(2), (4) Date: Dec. 2, 2013

(87) PCT Pub. No.: WO2013/000088
PCT Pub. Date: Jan. 3, 2013

(65) Prior Publication Data
US 2014/0120594 A1 May 1, 2014

Related U.S. Application Data

(60) Provisional application No. 61/501,873, filed on Jun. 28, 2011.

(51) Int. Cl.
| | | |
|---|---|---|
| C12P 7/10 | (2006.01) | |
| C02F 9/00 | (2006.01) | |
| C12P 7/16 | (2006.01) | |
| C02F 1/44 | (2006.01) | |
| C02F 3/28 | (2006.01) | |
| C02F 1/38 | (2006.01) | |
| C02F 3/30 | (2006.01) | |
| C02F 103/28 | (2006.01) | |
| C02F 1/28 | (2006.01) | |
| C02F 3/12 | (2006.01) | |
| C02F 1/04 | (2006.01) | |
| C02F 101/34 | (2006.01) | |
| C12P 5/02 | (2006.01) | |

(52) U.S. Cl.
CPC .............. *C12P 7/10* (2013.01); *C02F 9/00* (2013.01); *C12P 7/16* (2013.01); *C02F 1/04* (2013.01); *C02F 1/28* (2013.01); *C02F 1/38* (2013.01); *C02F 1/441* (2013.01); *C02F 1/444* (2013.01); *C02F 3/1268* (2013.01); *C02F 3/2853* (2013.01); *C02F 3/30* (2013.01); *C02F 2101/34* (2013.01); *C02F 2103/28* (2013.01); *C02F 2209/22* (2013.01); *C02F 2303/24* (2013.01); *C12P 5/023* (2013.01); *C12P 2203/00* (2013.01); *Y02E 50/16* (2013.01); *Y02W 10/15* (2015.05)

(58) Field of Classification Search
None
See application file for complete search history.

(56) References Cited

U.S. PATENT DOCUMENTS

| | | |
|---|---|---|
| 4,321,328 A | 3/1982 | Hoge |
| 4,412,867 A | 11/1983 | Cicuttini |
| 4,448,881 A | 5/1984 | Muller et al. |
| 5,177,008 A | 1/1993 | Kampen |
| 5,221,357 A | 6/1993 | Brink |
| 5,783,081 A | 7/1998 | Gaddy |
| 5,932,456 A | 8/1999 | Van Draanen et al. |
| 6,371,058 B1 * | 4/2002 | Tung .............. C02F 1/04 122/488 |
| 6,555,350 B2 | 4/2003 | Ahring et al. |
| 6,821,382 B1 | 11/2004 | Lundgren |
| 7,285,402 B2 | 10/2007 | Gaddy et al. |
| 7,569,146 B2 | 8/2009 | Peyton et al. |
| 8,017,365 B1 | 9/2011 | Rein et al. |
| 2002/0192774 A1 | 12/2002 | Ahring et al. |
| 2004/0187863 A1 | 9/2004 | Langhauser |
| 2006/0188965 A1 | 8/2006 | Wyman et al. |
| 2008/0064906 A1 * | 3/2008 | Foody .............. C12P 7/10 585/242 |
| 2009/0152208 A1 | 6/2009 | Agrawal |
| 2009/0263540 A1 | 10/2009 | Allen et al. |
| 2009/0286295 A1 | 11/2009 | Medoff et al. |
| 2010/0163396 A1 | 7/2010 | Michalek et al. |
| 2010/0261243 A1 | 10/2010 | Kloos |
| 2011/0020884 A1 | 1/2011 | Latouf et al. |

FOREIGN PATENT DOCUMENTS

| | | |
|---|---|---|
| CN | 1443141 A | 9/2003 |
| CN | 101580323 A | 11/2009 |
| WO | 2006/004748 | 1/2006 |
| WO | 2009/134745 | 11/2009 |
| WO | 2009/134791 | 11/2009 |
| WO | 2009/135276 | 11/2009 |
| WO | 2010/118369 | 10/2010 |
| WO | 2010/129637 | 11/2010 |

OTHER PUBLICATIONS

Merrick, Wastewater Treatment Options for the Biomass-To-Ethanol Process, Oct. 22, 1998.*
Barta et al., Techno-economic evaluation of stillage treatment with anaerobic digestion in a softwood-to-ethanol process, Biotechnology for Biofuels 2010, 3:21.*
Merrick'98, Merrick & Company, Wastewater Treatment Options for the Biomass-To-Ethanol Process, Oct. 22, 1998.*
Mohana et al., Journal of Hazardous Materials, vol. 163, pp. 12-25, 2009.*

(Continued)

*Primary Examiner* — Louise W Humphrey
*Assistant Examiner* — Srikanth Patury
(74) *Attorney, Agent, or Firm* — Venable LLP

(57) ABSTRACT

Disclosed herein is a process for recycling water in a cellulosic conversion process that comprises selecting process stream(s) that may contain reduced levels of inhibitors and subsequently subjecting the stream(s) to a treatment process to produce treated water. The treated water is thereafter recycled to the cellulosic conversion process, associated utilities or the seal water system. The process streams selected for treatment may comprise less than 5 wt % organic content and/or less than 5 wt % inorganic content. The process of the invention comprises at segregating process streams based on their treatment requirements. The segregated process streams may be sent to respective separate treatments selected from anaerobic digestion, aerobic digestion, physical separation and chemical treatment.

21 Claims, 5 Drawing Sheets

(56) References Cited

OTHER PUBLICATIONS

Simate et al., Desalination, vol. 273, pp. 235-247, 2011.*
Aden et al., Lignocellulosic Biomass to Ethanol Process Design and Economics Utilizing Co-Current Dilute Acid Prehydrolysis and Enzymatic Hydrolysis for Corn Stover, Technical Report, NREL, Jun. 2002, (Year: 2002).*
Abrigo et al., "Recycling of Distillery Slops for Ethanol and Acetic Acid Production", The Philippine Agricultural Scientist, vol. 85, No. 2 (2002) 155-60.
Aden et al., "Lignocellulosic Biomass to Ethanol Process Design and Economics Utilizing Co-Current Dilute Acid Prehydrolysis and Enzymatic Hydrolysis for Corn Stover", NREL/TP-510-32438, Contract No. DE-AC36-99-GO10337 (2002).
Alzate et al., "Energy consumption analysis of integrated flowsheets for production of fuel ethanol from lignocellulosic biomass", Energy, vol. 31 (2006) 2447-59.
Bialas et al., Fuel ethanol production from granular corn starch using accharomyces cerevisiae in a long term repeated SSF process with full stillage recycling, Bioresource Technology, vol. 101 (2010) 3126-31.
Galbe et al., "Simulation of Ethanol Production Processes Based on Enzymatic Hydrolysis of Lignocellulosic Materials Using ASPEN PLUS", Applied Biochemistry and Biotechnology, vol. 34/35 (1992) 93-104.
Huffaker, "Protecting water resources in biofuels production", Water Policy, vol. 12 (2010) 129-34.
Ingledew, "Water reuse in fuel alcohol plants: effect on fermentation. Is a "zero Discharge" concept attainable?", The Alcohol Textbook, 4th Ed. (2003) 343-54.
Larsson et al., "Recirculation of Process Water in the Production of Ethanol from Softwood", Bioresource Technology, vol. 60 (1997) 143-51.
Lynd et al "How biotech can transform biofuels" Nature Biotechnology, vol. 26, No. 2 (2008) 169-72.
Mohagheghi et al., "Impact of Recycling Stillage on Conversion of Dilute Sulfuric Acid Pretreated Corn Stover to Ethanol", Biotechnology and Bioengineering, vol. 105, No. 5 (2009) 992-96.
Palmqvist et al., "Design and Operation of a Bench-Scale Process Development Unit for the Production of Ethanol from Lignocellulosics", Bioresource Technology, vol. 58 (1996) 171-79.
Steinwinder et al., "Process Design of Wastewater Treatment for the NREL Cellulosic Ethanol Model", NREL/SR-5100-51838, (2011) Contract No. DE-AC36-08GO28308.
Stenberg et al., "Recycling of Process Streams in Ethanol Production from Softwoods Based on Enzymatic Hydrolysis", Applied Biochemistry and Biotechnology, vol. 70-72 (1998) 697-708.
Taherzadeh et al., "Acid-Based Hydrolysis Processes for Ethanol from Lignocellulosic Materials: A Review, Bioethanol Review", BioResources, vol. 2, No. 3 (2007) 472-99.
Wilkie et al. "Stillage characterization and anaerobic treatment of ethanol stillage from conventional and cellulosic feedstocks", Biomass & Bioenergy, vol. 19 (2000) 63-102.
Zhang et al., "A novel full recycling process through two-stage anaerobic treatment of distillery wastewater for bioethanol production from cassava", J. Hazard. Mat., vol. 179 (2010) 635-41.
Nie, Y., et al., "A Project Example on Alcohol Production Wastewater Deep Treatment and Reuse", China Brewing, No. 22, pp. 68-70 (2008).
Pre-Examination Report issued in counterpart Brazilian Patent Application No. 112013033729-0, dated Jul. 2, 2019 (6 pages).
Office Action issued in counterpart Canadian Patent Application No. 2,838,756, dated Oct. 24, 2018 (3 pages).
Office Action issued in counterpart Canadian Patent Application No. 2,838,756, dated Mar. 16, 2018 (4 pages).

* cited by examiner

METHOD FOR REDUCING WATER USAGE IN A CELLULOSIC CONVERSION PROCESS

This application is a national stage application of PCT/CA2012/050438 having an international filing date of Jun. 28, 2012 which claims benefit of U.S. provisional application No. 61/501,873 filed Jun. 28, 2011, both of which are incorporated by reference herein.

TECHNICAL FIELD

The present invention relates to an improved process for reducing water requirements in a cellulosic conversion process.

BACKGROUND OF THE INVENTION

Lignocellulosic feedstock is a term commonly used to describe plant-derived biomass comprising cellulose, hemicellulose and lignin. Much attention and effort has been applied in recent years to the production of fuels and chemicals, primarily ethanol, from lignocellulosic feedstocks, such as agricultural wastes and forestry wastes, due to their low cost and wide availability.

The first chemical processing step for converting lignocellulosic feedstock to ethanol, or other fermentation products, involves breaking down the fibrous lignocellulosic material to liberate sugar monomers from the feedstock for conversion to a fermentation product in a subsequent step of fermentation.

There are various known methods for producing fermentable sugars from lignocellulosic feedstocks, the most prominent involving an acid or alkali pretreatment followed by hydrolysis of cellulose with cellulase enzymes and β-glucosidase. The purpose of the pretreatment is to increase the cellulose surface area, with limited conversion of the cellulose to glucose. Acid pretreatment typically hydrolyses the hemicellulose component of the feedstock to yield xylose, glucose, galactose, mannose and arabinose and this is thought to improve the accessibility of the cellulose to cellulase enzymes. The cellulase enzymes hydrolyse cellulose to cellobiose which is then hydrolysed to glucose by β-glucosidase.

After production of a stream comprising fermentable sugar from the lignocellulosic feedstock, the sugars are fermented to ethanol or other fermentation products. If glucose is the predominant substrate present, the fermentation is typically carried out with a yeast that converts this sugar and other hexose sugars present to ethanol, although bacteria are also known for such purpose. This conversion can be carried out by a variety of organisms, including *Saccharomyces* spp. The ethanol is recovered from the fermentation broth, or "beer", by distillation. A still bottoms stream comprising dissolved residual organic and inorganic components as well as suspended lignin solids remains after distillation.

Utilizing lignocellulosic feedstocks for ethanol production offers an attractive alternative to burning or land-filling them, which is a practice commonly employed in the agriculture sector. Another advantage of these feedstocks is that the lignin byproduct, which remains after the cellulose conversion process, can be used as a fuel to power the process instead of fossil fuels. Several studies have concluded that, when the entire production and consumption cycle is taken into account, the production of ethanol from lignocellulosic feedstocks generates close to zero greenhouse gases.

However, despite the foregoing advantages, there are still hurdles to be overcome in order to make cellulosic ethanol conversion processes more sustainable. Cellulosic ethanol facilities should be built at large scale to be economically viable, but this requires large amounts of feedstock and consequently large amounts of water. When fresh water requirements for the process are high, it is necessary for the plant to be located near a water source, which in turn reduces the options available for plant site selection. Moreover, treatment of the incoming water and handling and disposal of water effluent from the plant is costly. Zero liquid discharge to the environment would be highly desirable.

Water recycle has been suggested as a means to both reduce fresh water requirements and the amount of wastewater that must be disposed of. However, water recycle has its own set of shortcomings that must be addressed to make it economically feasible.

For instance, recycling streams can increase the levels and/or the nature of the inhibitors in the process, thereby negatively impacting the ethanol production process. The pretreated streams generated during an acidic or basic lignocellulosic pretreatment process contain a number of compounds that are inhibitory to the enzymes used for enzymatic hydrolysis and the microorganisms used for ethanol fermentation (collectively referred to herein as "biocatalysts"). These inhibitory compounds may be inorganic or organic, suspended or dissolved, identified or unidentified and may have additive or synergistic impacts on the biocatalysts. Even if the biocatalysts have been acclimatized to the inhibitors present in process streams, further increases in the concentration of these inhibitors, or the introduction of different inhibitors to process streams containing pre-existing inhibitors, may increase the overall stress on the biocatalysts to the point that their performance is severely impacted.

One potent class of inhibitors generated during cellulosic ethanol conversion processes is phenolic compounds. When plant biomass is pretreated in a cellulosic ethanol process prior to enzymatic hydrolysis, simple or oligomeric phenolics and derivatives can be generated from lignin modification and/or degradation. These compounds are a known inhibitor for biomass-converting enzymes. Examples of phenolic compounds which have been demonstrated to be inhibitory to cellulose-degrading enzymes include vanillin, syringaldehyde, trans-cinnamic acid and hydroxybenzoic acid, as well as phenolic hydroxyl groups associated with lignin itself (Enzyme and Microbial Technology, Vol 46, Issues 3-4, pages 170-176; Journal of Biobased Materials and Bioenergy, Vol 2, No 1, pages 25-32). As these compounds inhibit the enzymes even at very low concentrations, any increase in the concentration, such as through recycle of streams containing these compounds in the process, would further impact the performance of the enzymes.

Another particularly potent inhibitor in cellulosic ethanol conversion processes is acetic acid, which is produced by the release of acetyl groups present on lignocellulosic feedstocks during chemical pretreatment. In particular, acetic acid is a known inhibitor of fermenting microorganisms employed to ferment glucose to ethanol. The microorganism is already inhibited by the natural levels of the acetic acid in the fermentation process, and any further increase in its levels, such as would be the case if streams which contain acetic acid were recycled in the process, would further impact the performance of the microorganism. Other potential inhibitors of biocatalysts generated during pretreatment include inorganic salts, hydroxymethylfurfural (HMF) and furfural.

Acetic acid poses an even larger challenge for cellulosic ethanol processes relative to conventional first generation ethanol processes (i.e., ethanol produced from corn not lignocellulosic feedstock), as the levels present in the streams are much higher. Kellsall and Lyons ("The Alcohol Textbook", Ed. K. Jaeques, T. P. Lyons and D. R. Kelsall, 1999, Nottingham University Press, Nottingham, United Kingdom, incorporated herein by reference) note that typical levels of acetic acid in a conventional corn ethanol fermentation range between 0.014 and 0.02 wt %. They further note that acetic acid can be produced by contaminants, and that levels at or above 0.05 wt % are known to be inhibitory to yeast. By contrast, in a cellulosic ethanol process, depending on the pretreatment conditions and the composition of the feedstock, acetic acid levels in the feed stream to fermentation can range from 0.1-1.2 wt %, which is between 6 and 70 times more concentrated than corn ethanol processes and above known inhibition levels. Cellulosic conversion processes are also susceptible to bacterial contamination, which can add more acetic acid due to production by the contaminating bacteria. With acetic acid levels already well above typical levels, any further acetic acid added through a recycle process would be detrimental to the process, and would require additional processing to manage, which would impact the economic viability of the process.

Washing steps after pretreatment can help reduce the levels of acetic acid, however adding more water to the process can impact the economics of the process, as the added water must later be removed. Another method that has been proposed to reduce the concentration of inhibitors is a process known as overliming, which involves the addition of lime to precipitate the inhibitors. However, the addition of lime produces gypsum, which is costly to dispose of, results in scale deposition, requires additional water usage and reduces sugar yield.

Anaerobic fermentation of still bottoms remaining after distillation, followed by re-circulation of effluent to the process is one of many potential options the inventors have identified for treating and recycling streams in cellulosic ethanol processes and can be a cost-effective option. However, anaerobic treatment systems are sensitive to the presence of high sulfate levels. In cellulosic conversion processes employing sulfuric acid pretreatment, sulfate salts are generated during adjustment of the pretreated feedstock with alkali. Alternatively, alkali pretreated feedstock can be treated with sulfuric acid prior to enzymatic hydrolysis, which also generates sulfate salts. Regardless of their source, if sulfate-rich streams are sent to anaerobic digesters prior to their recycle, complicated process steps are required to remove these salts prior to anaerobic treatment, which, in turn, can increase both the capital and operating costs of the process.

Thus, there is a need in the art for an improved process of water recycle in a cellulosic conversion process that reduces the build-up of inhibitors, while reducing capital and operating costs.

SUMMARY OF THE INVENTION

It is an object of the invention to reduce water requirements in a cellulosic conversion process.

Disclosed herein is a cellulosic conversion process employing water recycle that comprises obtaining process streams generated during the process that contain lower levels of inhibitors and/or other deleterious components relative to other process streams, and subsequently subjecting the process streams to a treatment process. The treatment process comprises feeding two or more process streams to separate respective treatments, wherein the particular stream(s) fed to each treatment is selected based on its specific treatment requirement, which in turn depends on the organic and inorganic components present in the stream(s). The resultant treated water stream or streams are thereafter recycled to the cellulosic conversion process, associated utilities, the seal water system or a combination thereof.

The two or more process streams subjected to the treatment process include spent cleaning solution used to clean process equipment utilized during the cellulosic conversion process; a process condensate stream obtained during the cellulosic conversion process; rectifier effluent from a distillation; a blowdown stream obtained from a cooling tower or boiler system; a regenerated stream; and spent seal water obtained from one or more pieces of equipment used during the cellulosic conversion process.

The processes disclosed herein have numerous benefits over conventional cellulosic conversion processes involving water recycle. Advantageously, by selecting the above process streams from the cellulosic conversion process for recycle that contain lower levels of inhibitors or other undesirable components and by segregating those process streams with similar treatment requirements, the overall treatment system requirements can be minimized. Stream segregation reduces the size of the treatment equipment only to what is necessary to provide treated water streams for recycle having inhibitor concentrations reduced to a level that does not have a significant impact on bio-catalyst (e.g., yeast and enzyme) performance. Thus, the invention allows the capital and operating costs of the process to be reduced, while maintaining the level of treatment of the process stream(s) that is required to meet recycle requirements of the process. The cellulosic conversion process may comprise the steps of pretreating a lignocellulosic feedstock, hydrolyzing cellulose in the pretreated feedstock to produce glucose, fermenting at least the glucose to produce a fermentation broth comprising an alcohol and distilling the alcohol to produce concentrated ethanol and still bottoms. Preferably, the alcohol is ethanol.

In one embodiment of the invention, the two or more process streams comprise at least a process condensate stream. The process condensate stream may be flash condensate or evaporator condensate. The flash condensate may result from a step of flashing conducted on the pretreated feedstock to decrease the temperature of same. The evaporated condensate may result from evaporating still bottoms in an evaporator unit and condensing vapour obtained therefrom. The step of obtaining the process stream may comprise combining two or more of the process streams.

In one aspect of the invention, the treatment process comprises at least a step of feeding one or more of the process streams to an anaerobic digestion and one or more of the process streams to an aerobic digestion. One or more treated water streams resulting from the treatment process are re-circulated to the cellulosic conversion process, associated utilities, seal water system or a combination thereof. The treated water stream(s) resulting from the treatment process may comprise either an effluent stream from the anaerobic digestion, an effluent stream from the aerobic digestion, both effluent streams, or one or more streams derived therefrom. The effluent stream from the anaerobic or aerobic digestion, or both effluent streams, may be further treated by one or more of reverse osmosis and filtration to remove sediment prior to the step of re-circulating.

In further embodiments, an effluent stream from the anaerobic digestion is fed to the aerobic digestion. A second effluent stream from the anaerobic digestion may be fed to a physical separation, a chemical separation or discharged from the process. The treated water stream(s) that is re-circulated may comprise an effluent stream from the aerobic digestion. The treatment may comprise the use of a second aerobic digestion, wherein an effluent stream from the second aerobic digestion, or one or more streams derived therefrom, is discharged from the process. The effluent stream from the anaerobic or aerobic digestion, or both effluent streams, may be further treated by one or more of reverse osmosis, ion exchange and filtration to remove sediment, ions or both sediment and ions prior to the step of re-circulating. The treatment process may further comprise subjecting the blowdown stream, the regenerated stream, the spent seal water stream, or a combination thereof, to a reverse osmosis or ion exchange operation.

In some embodiments of the invention, the treatment process reduces the concentration of acetic acid relative to the feed.

The treated water stream may be re-circulated to a cooling tower system, boiler feed water system, the seal water system, or any combination thereof. In further embodiments of the invention, the one or more treated water streams are re-circulated to the step of pretreating, hydrolyzing, fermenting, to a cleaning system, to residue processing stage or a combination thereof.

According to a further aspect of the present invention, the treatment process comprises feeding two or more process streams from the cellulosic conversion process to respective separate treatments selected from anaerobic digestion, aerobic digestion, physical separation and chemical treatment. The two or more process streams subjected to the treatment process are selected from spent cleaning solution used to clean process equipment utilized during the cellulosic conversion process; a process condensate stream obtained during the cellulosic conversion process; rectifier effluent from a distillation; a blowdown stream obtained from a cooling tower or boiler system; a regenerated stream; and spent seal water obtained from one or more pieces of equipment used during the cellulosic conversion process. One or more treated water streams resulting from the treatment process are then re-circulated to the cellulosic conversion process, associated utilities or seal water system. The two or more process streams sent to the separate treatments may each result from combining two or more of the aforesaid process streams.

According to one embodiment of this aspect of the invention, during the treatment process, three process streams are fed to respective separate treatments in the treatment process. According to a further embodiment of the invention, one of the process streams is discharged to the environment.

In certain embodiments of this aspect of the invention, some streams may be fed to an anaerobic digester and others fed to an aerobic digester. One or more treated streams obtained from either or both of the anaerobic and aerobic digestions are then re-circulated to the cellulosic conversion process, associated utilities or the seal water system. Prior to re-circulation, the foregoing treated streams may be treated further by aerobic digestion and/or a physical or chemical separation step, such as reverse osmosis, ion exchange or filtration.

In yet further embodiments of the invention, process streams from the cellulosic conversion process are fed to an anaerobic digestion, others are fed to an aerobic digestion, while others are fed to a chemical treatment step such reverse osmosis and/or ion exchange. Treated streams obtained from either or all of these treatment steps within the treatment process are then re-circulated to the cellulosic conversion process, associated utilities, the seal water system or a combination thereof. Prior to re-circulation, the foregoing treated streams may be treated further by aerobic digestion and/or a physical or chemical separation step, such as reverse osmosis, ion exchange or filtration.

According to a further aspect of the invention, there is provided a process for recycling water in a cellulosic conversion process that produces a fermentation product, the process comprising the steps of: (i) obtaining process streams for further treatment and recycle, wherein the process streams arise from the cellulosic conversion process, associated utilities or a seal water system; (ii) subjecting the process streams to a treatment process, thereby producing one or more treated water streams, the treatment process comprising: at least a step of feeding two or more of the process streams to respective separate treatments selected from anaerobic digestion, aerobic digestion, physical separation and chemical treatment, wherein the process streams comprise less than 5 wt % organic content and less than 5 wt % inorganic content; and (iii) re-circulating the one or more treated water streams to the cellulosic conversion process, associated utilities, seal water system or a combination thereof.

In one embodiment of the invention, one or more process streams, or one or more streams derived therefrom, are fed to aerobic digestion. Preferably, the one or more streams fed to aerobic digestion are spent cleaning solution, a process condensate stream, a rectifier effluent, spent seal water and a combination thereof.

DETAILED DESCRIPTION OF THE INVENTION

Figure 1:
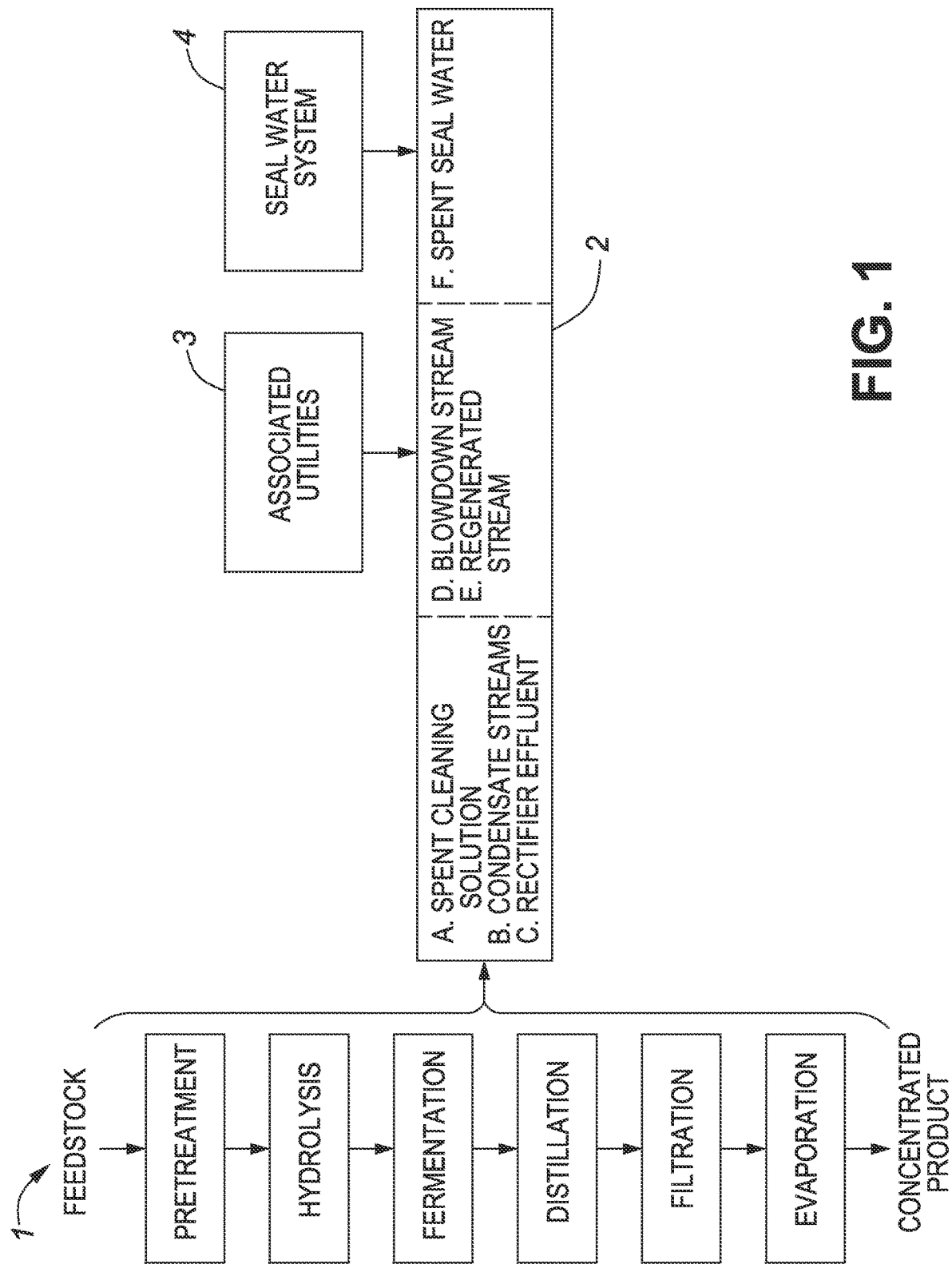
FIG. 1 depicts process streams that may be selected for treatment and recycle in a cellulosic conversion process to produce alcohol. The streams may be obtained from the conversion process itself, from the associated utilities and/or the seal water system.

The following description is of a preferred embodiment by way of example only and without limitation to the combination of features necessary for carrying the invention into effect. The headings provided are not meant to be limiting of the various embodiments of the invention. Terms such as "comprises", "comprising", "comprise", "includes", "including" and "include" are not meant to be limiting. In addition, the use of the singular includes the plural, and "or" means "and/or" unless otherwise stated. Unless otherwise defined herein, all technical and scientific terms used herein have the same meaning as commonly understood by one of ordinary skill in the art.

Description of Feedstock Types

By the term "cellulosic conversion process", it is meant a process for producing a fermentation product from a lignocellulosic feedstock, including, but not limited to, ethanol.

By the term "lignocellulosic feedstock", it is meant any type of plant biomass such as, but not limited to, non-woody plant biomass, cultivated crops such as, but not limited to grasses, for example, but not limited to, C4 grasses, such as switch grass, cord grass, rye grass, miscanthus, reed canary grass, or a combination thereof, sugar processing residues, for example, but not limited to, bagasse, such as sugar cane bagasse, beet pulp, or a combination thereof, residues remaining after grain processing, such as, but not limited to corn fiber, corn cobs after kernel removal, corn stover, or a combination thereof, agricultural residues, for example, but not limited to, soybean stover, corn stover, rice straw, sugar cane straw, rice hulls, barley straw, corn cobs, wheat straw, canola straw, oat straw, oat hulls, corn fiber, or a combination thereof, forestry biomass for example, but not limited to, recycled wood pulp fiber, sawdust, hardwood, for example aspen wood, softwood, or a combination thereof. Furthermore, the lignocellulosic feedstock may comprise lignocellulosic waste material or forestry waste materials such as, but not limited to, newsprint, cardboard and the like. Lignocellulosic feedstock may comprise one species of fiber or, alternatively, lignocellulosic feedstock may comprise a mixture of fibers that originate from different lignocellulosic feedstocks. In addition, the lignocellulosic feedstock may comprise fresh lignocellulosic feedstock, partially dried lignocellulosic feedstock, fully dried lignocellulosic feedstock, or a combination thereof. Moreover, new lignocellulosic feedstock varieties may be produced from any of those listed above by plant breeding or by genetic engineering.

Lignocellulosic feedstocks comprise cellulose in an amount greater than about 20%, more preferably greater than about 30%, more preferably greater than about 40% (w/w). For example, the lignocellulosic material may comprise from about 20% to about 50% (w/w) cellulose, or any amount therebetween. Furthermore, the lignocellulosic feedstock comprises lignin in an amount greater than about 10%, more typically in an amount greater than about 15% (w/w). The lignocellulosic feedstock may also comprise small amounts of sucrose, fructose and starch.

Feedstock Size Reduction

The lignocellulosic feedstock is generally first subjected to size reduction by methods including, but not limited to, milling, grinding, agitation, shredding, compression/expansion, or other types of mechanical action. According to the invention, the lignocellulosic feedstock from the size reduction process produces a size-reduced feedstock comprising particles of a defined length. At least 90% by weight of the particles in the size reduced feedstock may have a length less than between about ⅛ and about 6 inches. As would be appreciated by those of ordinary skill in the art, lignocellulosic feedstock that has been subjected to size reduction comprises feedstock particles having a range of sizes and shapes.

Size reduction by mechanical action can be performed by any type of equipment adapted for the purpose, for example, but not limited to, hammer mills, tub-grinders, roll presses, refiners, shredders and hydrapulpers. It should be appreciated that the lignocellulosic feedstock need not be subjected to size reduction if the particle size of the feedstock is already between ½ to 6 inches.

If size reduction is required, it can be performed while the lignocellulosic feedstock is dry or moist, i.e., having a moisture content of 0% to about 20%, or while water is added to the lignocellulosic feedstock. Dry shredding can be carried out, for example, with an SSI or Grizzly grinder, hammer mill or tub grinder, while wet shredding may be performed with pulpers. When dry shredding is employed, the particle size may be between about ½ to about 6 inches. When hammer milling, the particle size may be less than about 4 inches to less than about ½ inch depending on the size of the screens used in the hammer mill.

The size of the lignocellulosic feedstock particles can have an impact on both processing of the feedstock and in the chemical reactions involved during pretreatment. A person of ordinary skill in the art could select a concentration of feedstock particles and particle characteristics that allows for ease of processing and that achieves a desired reactivity of the feedstock in pretreatment.

For the purposes of this specification, the size of the feedstock particles is determined by image analysis using techniques known to those of ordinary skill in the art. An example of a suitable image analysis technique is disclosed in Igathinathane (Sieveless particle size distribution analysis of particulate materials through computer vision, Computers and Electronics in Agriculture, 2009, 66:147-158), which reports particle size analyses of several different hammer milled feedstocks. The measurement may be a volume or a weight average length.

Washing of the feedstock may be carried out to remove sand, grit and other foreign particles as they can cause damage to the downstream equipment.

Feedstock Slurry Preparation

Slurrying of the feedstock allows it to be pumped readily and may be carried out in any suitable batch or continuous mixing vessel, including a standpipe or pulper. Slurrying may be distinct from the water and chemical addition or may occur simultaneously therewith.

Slurrying can occur at any suitable consistency selected by those of ordinary skill in the art. However, in practice, the consistency of the feedstock slurry utilized will depend on the specific mixing means employed and the specific pumps used. In one embodiment of the invention, the consistency of the feedstock slurry is between about 2 wt % and about 40 wt % or more typically between about 4 wt % and about 20 wt %.

The consistency of the aqueous slurry of the lignocellulosic feedstock is expressed as the undissolved solids concentration (UDS). Reference may be made to the "Handbook of Industrial Mixing" (Ed. Paul, Atiemo-Obeng, Kresta, 2004, Wiley-Interscience, Hoboken, N.J., incorporated herein by reference), which provides an introduction to the equipment and critical parameters of mixing performance and design. (See, for example, Chapters 10, 17 and 18 that particularly focus on solid-liquid mixing).

Dewatering Prior to Pretreatment

After slurrying, leaching and/or soaking, the lignocellulosic feedstock may subsequently be dewatered by any suitable technique known to those of ordinary skill in the art. For instance, dewatering may be effected by utilizing devices that remove water under pressure from the aqueous feedstock slurry. Dewatering devices suitable for use in the invention include pressurized screw presses, such as those described in WO 2010/022511 (incorporated herein by reference) and pressurized filters. The dewatering process optionally includes a pre-draining zone in order to drain out water from the feedstock slurry at atmospheric pressure or higher. This dewatered feedstock slurry is then sent to one or more devices for dewatering the slurry under pressure. Water expressed from the lignocellulosic feedstock by the dewatering step may be reused in the process.

Pretreatment of the Lignocellulosic Feedstock

As used herein, a "pretreated lignocellulosic feedstock" or "pretreated feedstock" is a lignocellulosic feedstock that has been subjected to physical and/or chemical processes to make the fiber more accessible and/or receptive to the actions of cellulolytic enzymes or to subsequent chemical treatment to hydrolyze cellulose.

The pretreatment generally disrupts the fiber structure of the lignocellulosic feedstock and increases the surface area of the feedstock to make it accessible to cellulase enzymes. Preferably, the pretreatment is performed so that a high degree of hydrolysis of the xylan and only a small amount of conversion of cellulose to glucose occurs. The cellulose is hydrolyzed to glucose in a subsequent step that uses cellulase enzymes.

The extent of xylan hydrolysis may be between about 80 and 100 wt %, or any range therebetween. A suitable pH and temperature can be selected within this pH range to hydrolyze at least about 80% of the xylan, while maintaining the degree of cellulose hydrolysis at about 3 to about 15 wt %.

The acid pretreatment is preferably carried out at a temperature of about 160° C. to about 280° C. It should be understood that, in practice, there will be a time delay in the pretreatment process before the feedstock reaches this temperature range. Thus, the above temperatures correspond to those values reached after sufficient application of heat to reach a temperature within this range. The time that the feedstock is held at this temperature may be about 6 seconds to about 3600 seconds, or about 15 seconds to about 750 seconds or about 30 seconds to about 240 seconds.

The pretreatment is typically carried out under pressure. For example, the pressure during pretreatment may be between about 50 and about 700 psig or between about 75 and about 600 psig, or any pressure range therebetween.

If acid is employed for pretreatment, it may be sulfuric acid, sulfurous acid, hydrochloric acid or phosphoric acid. Preferably, the acid is sulfuric acid. The amount of acid added to the lignocellulosic feedstock may vary, but should be sufficient to achieve a final concentration of acid in the slurry of about 0.02 wt % to about 2 wt %, or any amount therebetween. The resulting pH of the feedstock is about pH 0.4 to about pH 3.5, or any pH range therebetween. The feedstock may be heated with steam during or prior to pretreatment. Without being limiting, one method to carry this out is to use low pressure steam to partially heat the feedstock, which is then pumped to a heating train of several stages. Other means may be employed to heat the feedstock, such as commercially available mixing devices designed for introducing steam and optionally acid through spray nozzles.

Without being limiting, pretreating of the feedstock slurry preferably involves continuous pretreatment, meaning that the lignocellulosic feedstock is pumped through a reactor continuously. Continuous acid pretreatment is familiar to those skilled in the art; see, for example, WO 2006/128304 (Foody and Tolan).

The use of organic liquids in pretreatment may be used in the invention as described by Converse et al., (U.S. Pat. No. 4,556,430) and has the advantage that the low boiling point liquids can easily be recovered and reused. Other pretreatments, such as the Organosolv™ process, also use organic liquids.

The acid pretreatment produces a composition comprising an acid pretreated feedstock. Sugars produced by the hydrolysis of hemicellulose during acid pretreatment are generally present in the composition and include xylose, glucose, arabinose, mannose, galactose or a combination thereof. Organic acids may be present in the composition as well and may include acetic acid, galacturonic acid, formic acid, lactic acid, glucuronic acid or a combination thereof. Many lignocellulosic feedstocks contain hemicellulose with acetyl groups attached to xylan. Pretreatment processes liberate acetic acid from the acetyl groups.

According to one exemplary embodiment of the invention, the soluble components of the pretreated feedstock composition are separated from the solids. This separation may be carried out by washing the pretreated feedstock composition with an aqueous solution to produce a wash stream, and a solids stream comprising the unhydrolyzed, pretreated feedstock and/or by using solids-liquid separation techniques. The aqueous stream, which includes the sugars released during pretreatment, the pretreatment chemical and other soluble components, may then be fermented using a microorganism capable of fermenting the sugars derived from the hemicellulose component of the feedstock.

Pretreatment may also be carried out under alkaline conditions. Examples of suitable alkaline pretreatment processes include ammonia fiber expansion (AFEX) or dilute ammonia pretreatment.

According to the AFEX process, the cellulosic biomass is contacted with ammonia or ammonium hydroxide, which is typically concentrated, in a pressure vessel. The contact is maintained for a sufficient time to enable the ammonia or ammonium hydroxide to swell (i.e., decrystallize) the cellulose fibers. The pressure is then rapidly reduced which allows the ammonia to flash or boil and explode the cellulose fiber structure. The flashed ammonia may then be recovered according to known processes. The AFEX process may be run at about 20° C. to about 150° C. or at about 20° C. to about 100° C. and all temperatures therebetween. The duration of this pretreatment may be about 1 minute to about 20 minutes, or any time therebetween.

Dilute ammonia pretreatment utilizes more dilute solutions of ammonia or ammonium hydroxide than AFEX. Such a pretreatment process may or may not produce any monosaccharides. Dilute ammonia pretreatment may be conducted at a temperature of about 100 to about 150° C. or any temperature therebetween. The duration for such a pretreatment may be about 1 minute to about 20 minutes, or any time therebetween.

The concentration of pretreated lignocellulosic feedstock in the slurry depends on the particle size, water retention, pump capacity and other properties of the feedstock. Typically, the concentration is between about 3% and about 30% (w/w), or any amount therebetween of fiber solids (also known as suspended or undissolved solids), or between about 10% and about 30% (w/w) fiber solids, or any amount therebetween. The fiber solids concentration may depend on whether dewatering of the feedstock slurry is carried out prior to pretreatment, for example as set forth in WO 2010/022511 (incorporated herein by reference).

Subsequent to pretreatment, the pretreated feedstock slurry is typically cooled to decrease its temperature to a range at which the cellulase enzymes are most active. Cooling of the feedstock can occur in a number of stages utilizing flashing, heat exchange or other suitable means.

Flashing removes steam and volatiles from the system. For example, from 1 to about 8 successive flashing stages, or any amount therebetween, can be performed. The multiple flashing stages generate flash steam at different pressures. The steam from flashing can be used as a source of steam in the plant. For example, flash steam may supply steam to a downstream evaporator unit or be used for cleaning or disinfecting.

Steam from the flash tanks may also be used to indirectly preheat process streams, resulting in the production of flash condensate. For example, flash steam may be used on one side of a heat exchanger to preheat boiler feed water on the other side of the heat exchanger, thereby producing preheated boiler feed water and flash condensate. Similarly, the flash condensate itself can also be used to indirectly preheat process stream. Flash steam may also be cooled with cooling water, chilled water, or other sources of water to produce flash condensate if it is not convenient to preheat other streams. Once created, the flash condensate may then be sent to the treatment process of the invention, as described below.

Enzymatic Hydrolysis and Enzyme Fermentation

The enzymatic hydrolysis of the cellulose to soluble sugars can be carried out with any type of cellulase enzymes suitable for such purpose and effective at the pH and other conditions utilized, regardless of their source. Among the most widely studied, characterized and commercially produced cellulases are those obtained from fungi of the genera *Aspergillus, Humicola, Chrysosporium, Melanocarpus, Myceliophthora, Sporotrichum* and *Trichoderma*, and from the bacteria of the genera *Bacillus* and *Thermobifida*. Cellulase produced by the filamentous fungi *Trichoderma longibrachiatum* comprises at least two cellobiohydrolase enzymes termed CBHI and CBHII and at least four EG enzymes. As well, EGI, EGII, EGIII, EG V and EGVI cellulases have been isolated from *Humicola insolens* (see Lynd et al., 2002, Microbiology and Molecular Biology Reviews, 66(3):506-577 for a review of cellulase enzyme systems and Coutinho and Henrissat, 1999, "Carbohydrate-active enzymes: an integrated database approach." In Recent Advances in Carbohydrate Bioengineering, Gilbert, Davies, Henrissat and Svensson eds., The Royal Society of Chemistry, Cambridge, pp. 3-12, each of which are incorporated herein by reference).

The conversion of cellobiose to glucose is carried out by the enzyme β-glucosidase. By the term "β-glucosidase", it is meant any enzyme that hydrolyzes the glucose dimer, cellobiose, to glucose. The activity of the β-glucosidase enzyme is defined by its activity by the Enzyme Commission as EC#3.2.1.21. The β-glucosidase enzyme may come from various sources; however, in all cases, the β-glucosidase enzyme can hydrolyze cellobiose to glucose. The β-glucosidase enzyme may be a Family 1 or Family 3 glycoside hydrolase, although other family members may be used in the practice of this invention. The preferred β-glucosidase enzyme for use in this invention is the Bgl1 protein from *Trichoderma reesei*. It is also contemplated that the β-glucosidase enzyme may be modified to include a cellulose binding domain, thereby allowing this enzyme to bind to cellulose.

In addition to CBH, EG and beta-glucosidase, there are several accessory enzymes that aid in the enzymatic digestion of cellulose (see co-owned WO 2009/026722 (Scott), which is incorporated herein by reference, and Harris et al., 2010, Biochemistry, 49:3305-3316). These include EGIV, also known as Cel61, swollenin, expansin, lucinen and cellulose-induced protein (Cip). Glucose can be enzymatically converted to the dimers gentiobiose, sophorose, laminaribiose and others by beta-glucosidase via transglycosylation reactions.

Cellulase enzyme mixtures used to hydrolyze cellulose are produced in an enzymatic fermentation. The fermentation to produce the cellulase enzymes can be conducted with any of the previously mentioned organisms. The fermentation may be conducted in an enzyme production facility located in close proximity to the ethanol production facility, such that the enzyme product can be transported via pipeline to the ethanol production facility. Alternatively, the enzyme production facility may be in a different geographical location from the ethanol production facility, with the enzyme product being shipped to the ethanol production facility.

The enzymatic fermentation requires both an organic carbon source as well as nutrients necessary to support growth and enzyme production. It may be a simple or complex carbon source, purified or unpurified, containing carbon source(s) including, but not limited to, glucose, xylose, mannose, galactose, fructose, sucrose, dextrose, glycerol, or methanol. The carbon source will also generally contain a secondary carbon source that induces enzyme production from the fermenting organism. Some examples of inducing compounds include but are not limited to cellulose, cellobiose, gentiobiose and sophorose.

The nutrients required for growth and enzyme production are those typically associated with the growth of any microbial fermentation. For example, nutrients added to the fermentation may include yeast extract, corn steep liquor, specific amino acids, phosphate, nitrogen sources, salts, trace elements and vitamins.

The fermentation process is typically a sterile process, meaning all components of the fermentation equipment and media ingredients that come in contact with the fermentation broth are heat treated with steam, either directly or indirectly, to eliminate the presence of any microorganisms other than the production microorganism. The fermentation may be operated in a fed-batch or continuous mode.

The fermentation is generally conducted at a temperature of about 20° C. to about 45° C., or between about 25° C. and about 35° C., or any temperature therebetween and at a pH of between about 3.0 and about 6.0 or between about 3.5 and about 5.5, or any pH therebetween. Furthermore, the fermentation is generally operated in an aerobic regime, with sterile-filtered air supplied to the vessel to maintain a dissolved oxygen level in the vessel that is measured above 0%. For example, the dissolved oxygen level, as measured in the fermentation broth at any point during the fermentation process may be between about 1% and about 90% of saturation.

Once the enzyme fermentation is complete, the broth containing both enzymes and biomass of the fermenting organism is transferred to a storage vessel. From there, depending on the location of the enzyme production facility, and the location of the ethanol facility, the broth can be transferred directly to the ethanol facility for use in the hydrolysis system through a pipeline. Alternatively, the fermentation broth can be further processed before being sent to the ethanol production facility for use in the hydrolysis system.

Further processing steps may be conducted to change any number of characteristics in the enzyme product stream as per requirements of the ethanol production facility or other uses thereof. This includes, but is not limited to, separating the enzyme from the fermenting organism in the enzyme product stream, reducing the concentration of other microorganisms in the product stream, increasing the concentration of enzyme in the product stream through concentration and reducing the concentration of other components in the stream, such as unconsumed components. Measures may be taken to improve storage and shelf life, including stabilizing the product stream by the addition of sucrose, glycerol and sorbitol, preserving the product stream to improve shelf life or packaging the enzyme into discrete containers for transport to the ethanol facility and/or for prolonged storage. Equipment used to further process the product stream may include, but is not limited to, filter presses, plate and frame presses, centrifuges, decanters, microfilters, ultrafilters, and reverse osmosis units. Components that may be added to the enzyme product stream may include, but are not limited, to sodium benzoate, potassium sorbate, phosphoric acid, sodium hydroxide, caramel colour, and sucrose.

The enzyme produced in the fermentor is then used to hydrolyze cellulose in the pretreated feedstock. The amount of enzyme supplied to the ethanol production facility depends on the production rate of the ethanol production facility, and the activity of the enzyme being supplied. An appropriate cellulase dosage can be about 1.0 to about 40.0 Filter Paper Units (FPU or IU) per gram of cellulose, or any amount therebetween. The FPU is a standard measurement familiar to those skilled in the art and is defined and measured according to Ghose (Pure and Appl. Chem., 1987, 59:257-268; which is incorporated herein by reference). A preferred cellulase dosage is about 10 to about 20 FPU per gram cellulose.

The enzymatic hydrolysis is generally conducted at a pH between about 4.0 and about 6.0 as this is within the optimal pH range of most cellulases. If acid pretreatment is utilized, the pH of the feedstock will be increased with alkali to about pH 4.0 to about 6.0 prior to enzymatic hydrolysis, or more typically between about 4.5 and about 5.5. However, cellulases with pH optima at more acidic and more alkaline pH values are known.

The alkali can be added to the pretreated feedstock after it is cooled, before cooling, or at points both before and after cooling. The alkali may be added in-line to the pretreated feedstock, such as an in-line mixer, to a pump downstream of pretreatment or directly to a hydrolysis vessel. The point of alkali addition can coincide with the cellulase enzyme addition, or it can be added upstream or downstream of the location of the enzyme addition.

The temperature of the slurry is adjusted so that it is within the optimum range for the activity of the cellulase enzymes. Generally, a temperature of about 45° C. to about 70° C., or about 45° C. to about 65° C., or any temperature therebetween, is suitable for most cellulase enzymes. However, the temperature of the slurry may be higher for thermophilic cellulase enzymes.

In order to maintain the desired hydrolysis temperature, the hydrolysis reactors may be jacketed with steam, hot water, or other heat sources. Moreover the reactors may be insulated to retain heat.

It is preferred that enzymatic hydrolysis and fermentation are conducted in separate vessels so that each biological reaction can occur at its respective optimal temperature. However, the hydrolysis of the invention may be conducted simultaneously with fermentation in a simultaneous saccharification and fermentation (SSF). SSF is typically carried out at temperatures of 35-38° C., which is a compromise between the 50° C. optimum for cellulase and the 28° C. optimum for yeast. Consequently, this intermediate temperature can lead to substandard performance by both the cellulase enzymes and the yeast.

Other design parameters of the hydrolysis system may be adjusted as required. For example, the volume of a hydrolysis reactor in a cellulase hydrolysis system can range from about 100,000 L to about 30,000,000 L, for example, between about 200,000 and about 20,000,000 L, or any volume therebetween, although reactors of large volume may be preferred to reduce cost. The total residence time of the slurry in a hydrolysis system may be between about 12 hours to about 200 hours, or any amount therebetween.

After the hydrolysis is complete, the product is glucose and any unreacted cellulose. Insoluble solids present in the resulting stream, including lignin, may be removed using conventional solid-liquid separation techniques prior to any further processing. However, it may be desirable in some circumstances to carry forward both the solids and liquids in the sugar stream for further processing.

Fermentation

Fermentation of glucose resulting from the hydrolysis may produce one or more of the fermentation products selected from an alcohol, a sugar alcohol, an organic acid and a combination thereof.

In one embodiment of the invention, the fermentation product is an alcohol, such as ethanol or butanol. For ethanol production, the fermentation is typically carried out with a *Saccharomyces* spp. yeast. Glucose and any other hexoses present in the sugar stream may be fermented to ethanol by wild-type *Saccharomyces cerevisiae*, although genetically modified yeasts may be employed as well, as discussed below. The ethanol may then be distilled to obtain a concentrated ethanol solution. Butanol may be produced from glucose by a microorganism such as *Clostridium acetobutylicum* and then concentrated by distillation.

The fermentation comprises at least fermenting glucose to ethanol. Xylose and arabinose that are derived from the hemicellulose may additionally be fermented to ethanol by a yeast strain that naturally contains, or has been engineered to contain, the ability to ferment these sugars to ethanol. Examples of microbes that have been genetically modified to ferment xylose include recombinant *Saccharomyces* strains into which has been inserted either (a) the xylose reductase (XR) and xylitol dehydrogenase (XDH) genes from *Pichia stipitis* (U.S. Pat. Nos. 5,789,210, 5,866,382, 6,582,944 and 7,527,927 and European Patent No. 450530) or (b) fungal or bacterial xylose isomerase (XI) gene (U.S. Pat. Nos. 6,475,768 and 7,622,284). Examples of yeasts that have been genetically modified to ferment L-arabinose include, but are not limited to, recombinant *Saccharomyces* strains into which genes from either fungal (U.S. Pat. No. 7,527,951) or bacterial (WO 2008/041840) arabinose metabolic pathways have been inserted.

Organic acids that may be produced during the fermentation include lactic acid, citric acid, ascorbic acid, malic acid, succinic acid, pyruvic acid, hydroxypropanoic acid, itaconoic acid and acetic acid. In a non-limiting example, lactic acid is the fermentation product of interest. The most well-known industrial microorganisms for lactic acid production from glucose are species of the genera *Lactobacillus, Bacillus* and *Rhizopus*.

Moreover, xylose and other pentose sugars may be fermented to xylitol by yeast strains selected from the group consisting of *Candida, Pichia, Pachysolen, Hansenula, Debaryomyces, Kluyveromyces* and *Saccharomyces*. Bacteria are also known to produce xylitol, including *Corynebacterium* sp., *Enterobacter liquefaciens* and *Mycobacterium smegmatis*.

The fermentation is typically conducted at a pH between about 4.0 and about 6.0, or between about 4.5 and about 6.0. To attain the foregoing pH range for fermentation, it may be necessary to add alkali to the stream comprising glucose. A temperature range for the fermentation of glucose to ethanol can be between about 18° C. and about 35° C.

In one exemplary embodiment of the invention, the operating temperature and pH of the fermentation is a balance between the optimum for the fermenting microorganism and conditions suitable for contamination management. The fermentation may also be supplemented with additional nutrients required for the growth of the fermentation microorganism. For example, yeast extract, specific amino acids, phosphate, nitrogen sources, salts, trace elements and vitamins may be added to the hydrolysate slurry to support their growth.

The fermentation may be conducted in batch, continuous or fed-batch modes with or without agitation. Preferably, the fermentation reactors are agitated lightly with mechanical agitation. A typical, commercial-scale fermentation may be conducted using multiple reactors. The fermentation microorganisms may be recycled back to the fermentor or may be sent to distillation without recycle. If recycle of the yeast is desirable, then a filtration step, as described below, is conducted prior to the fermentation to remove suspended solids from the hydrolysate, thereby enabling recycle of the yeast within fermentation.

Distillation

If ethanol or butanol is the fermentation product, the recovery is carried out by distillation, typically with further concentration by molecular sieves or membrane extraction. If there is no cell recycle in fermentation, the fermentation broth that is sent to distillation is a dilute alcohol solution containing solids, including unconverted cellulose, and any components added during the fermentation to support growth of the microorganisms. If cell recycle is employed in fermentation, then the fermentation broth will not contain a significant level of suspended solids.

Microorganisms are potentially present during the distillation depending upon whether or not they are recycled during the fermentation. The broth is preferably degassed to remove carbon dioxide and then pumped through one or more distillation columns to separate the alcohol from the other components in the broth. The mode of operation of the distillation system depends on whether the alcohol has a lower or a higher boiling point than water. Most often, the alcohol has a lower boiling point than water, as is the case when ethanol is distilled.

The column(s) in the distillation unit is preferably operated in a continuous mode, although it should be understood that batch processes are also encompassed by the present invention. Heat for the distillation process may be introduced at one or more points either by direct steam injection or indirectly via heat exchangers. The distillation unit may contain one or more separate beer and rectifying columns, in which case dilute beer is sent to the beer column where it is partially concentrated. From the beer column, the vapour goes to a rectification column for further purification. Alternatively, a distillation column is employed that comprises an integral enriching or rectification section.

An aqueous stream(s) remaining after ethanol distillation and containing solids, referred to herein as "still bottoms", is withdrawn from the bottom of one or more of the column(s) of the distillation unit. This stream will contain inorganic salts, unfermented sugars and organic salts. Lignin may be present as well if it is not removed prior to distillation.

When the alcohol has a higher boiling point than water, such as butanol, the distillation is run to remove the water and other volatile compounds from the alcohol. The water vapor exits the top of the distillation column and is known as the "overhead stream".

Alcohol Concentration

After ethanol distillation, the remaining water is removed from the alcohol-enriched vapour by an azeotropic breaking process to produce a concentrated alcohol solution. The term azeotropic breaking process or azeotrope breaking system is meant to encompass any process for breaking the azeotrope of the alcohol-enriched vapour. This includes, but is not limited to, feeding the alcohol-enriched vapour to molecular sieves. Other azeotropic breaking processes that are encompassed by this definition include pervaporation and the addition of benzene or cyclohexane to a distillation column. After breaking the azeotrope to obtain the concentrated alcohol solution, the vapour is typically condensed to product alcohol and then denatured. If benzene or cyclohexane is used to break the azeotrope, they may be added to a distillation column to which the alcohol-enriched vapour is fed and acid may be added into such distillation column to reduce the concentration of ammonia in the alcohol-enriched vapour within said distillation column.

Preferably, the azeotropic breaking process utilizes molecular sieves. In this case, reducing the concentration of ammonia in the alcohol-enriched vapour stream reduces or prevents fouling or capacity loss of the desiccant. Any of a variety of known molecular sieves (also referred to as molecular sieve dehydrators) may be used in the practice of the invention. Molecular sieves on the market contain a zeolite material that have a crystalline lattice structure that contains openings (pores) of a precise size, usually measured in angstroms (Å). Pore sizes that are suitable will depend on the alcohol to be concentrated. Preferred zeolites for use with ethanol-enriched vapour are those of type 3 Å since the pores are 3 Å in diameter while water molecules are 2.8 Å and ethanol molecules are 4.4 Å. Furthermore, other adsorbent materials besides zeolites are available that have an affinity for water such as activated alumina. Although these adsorbents may be utilized in the practice of the invention, zeolite materials are preferred since they are typically more selective.

As would be appreciated by those of skill in the art, molecular sieves commonly use "pressure swing adsorption" to remove water from a vapourized feed stream. This refers to the fact that the molecular sieve uses a relatively high pressure when water is being removed from the feed stream and a relatively low pressure when the molecular sieve desiccant is being regenerated, i.e., having water removed from the desiccant. Typical commercial designs have two or more beds of desiccant and cycle the vapour flow through the beds to provide continuous operation. (See Development and operation of the molecular sieve: an industry standard, R. L. Bibb Swain, The Alcohol Textbook, $4^{th}$ Edition, Nottingham University Press, 2003, pages 337-342). For example, during operation, a molecular sieve may be drying the feed vapour, while another is being regenerated (i.e., water is removed so that the desiccant is ready for the next feed cycle).

Still Bottoms Processing

If the still bottoms from distillation comprise lignin, they may be subjected to lignin separation to remove lignin and other converted undissolved solids therefrom. Lignin separation may be conducted by utilizing a filter press, or other known solids-liquid separation equipment. The separated lignin may be subsequently sent to a boiler.

Still bottoms from distillation may be sent to an evaporator unit. If the still bottoms are subjected to the lignin separation step, the separated liquid component may be fed to the evaporation unit. Here, the still bottoms are concentrated and the evaporated liquid is condensed by cooling. The evaporator condensate, in turn, may be sent to the treatment process, and then recycled, as discussed in more detail below. Typically, the evaporator condensate is cooled prior to the treatment process, with the heat optionally used to preheat a process stream elsewhere in the process.

The evaporator condensate may be combined with other condensates and process streams. The condensates are typically collected in a tank.

The still bottoms contain components that can be recovered as co-products, as discussed below. Evaporation of the still bottoms can allow for more efficient extraction of these co-products.

In one embodiment of the invention, the evaporator unit is a multiple-effect evaporator. The evaporation may be carried out in a single-stage evaporator or may be part of a multiple-effect system, i.e., a system in which more than one evaporator is employed. Multiple-effect evaporator systems are preferred as they can reduce heating requirements and the resultant energy usage. A total of 3 to 7 effects are preferred to achieve the optimum steam economy. A multiple-effect evaporator system utilized in accordance with the invention can be forward fed, meaning that the feeding takes place so that the solution to be concentrated enters the system through the first effect, which is at the highest temperature. Partial concentration occurs in the first effect, with vapour sent to the second effect to provide heat for same. The partially concentrated solution is then sent to the second effect where it is again partially concentrated, with vapour sent to the third effect, and so on. Alternatively, backward feeding may be utilized, in which the partially concentrated solution is fed from effect to effect with increasing temperature.

Those of skill in the art can readily choose a suitable operating temperature for the evaporator unit. In embodiments of the invention, the operating temperature of the evaporator unit can be between about 40° C. and about 145° C. It will be understood that the temperature is measured under the operating pressure, which is typically under vacuum or at atmospheric pressure, but can be at higher pressure. Co-products can be recovered from the condensate. For example, acetic acid can be recovered from the condensate by liquid-liquid extraction using conventional processes. This technique may involve using a solvent to extract acetic acid from the feed stream, followed by distillation stages for dehydration, solvent recovery and acid purification. One or more of the bottom products from these distillation stages can be sent to the anaerobic digester and then water obtained from the anaerobic treatment can be recycled into the process.

Inhibitors

As discussed, streams derived from lignocellulosic feedstocks contain a number of compounds that are inhibitory to the microorganism in the fermentation or cellulase enzymes. Furan derivatives such as 2-furaldehyde (furfural) and 5-hydroxymethyl-2-furaldehyde (HMF) are inhibitory compounds that originate from the breakdown of the carbohydrate fraction, namely xylose and glucose, respectively. Additional organic acids found in the process streams that may be inhibitory to yeast or other microorganisms include galacturonic acid, lactic acid, glucuronic acid, 4-O-methyl-D-glucuronic acid or a combination thereof. Inhibiting phenolic compounds are also produced by the degradation of lignin, which include vanillin, syringaldeyhde, and hydroxybenzylaldehyde. In particular, vanillin and syringaldehyde are produced via the degradation syringyl propane units and guaiacylpropane units of lignin (Jönsson et al., 1998, Appl. Microbiol. Biotechnol. 49:691).

Acetic acid is a component of process streams produced from lignocellulosic material that is highly inhibitory to yeast and cellulase enzymes. The acetate arises from acetyl groups attached to xylan and lignin that are liberated as acetic acid and/or acetate by exposure to acid or other chemicals that hydrolyze the feedstock. (Abbott et al., 2007, FEMS Yeast Res. 7:819-833; Hu et al., 2009, Bioresource Technology 100:4843-4847; and Taherzadeh et al., 1997, Chem Eng Sci, 52:2653-5659).

Kellsall and Lyons ("The Alcohol Textbook", Ed. K. Jaeques, T. P. Lyons and D. R. Kelsall, 1999, Nottingham University Press, Nottingham, United Kingdom, incorporated herein by reference) disclose that acetic acid levels at or above 0.05 wt % are known to be inhibitory to yeast. However, the inhibition in cellulosic conversion processes to produce ethanol or other fermentation products is a more significant problem than corn ethanol fermentation as, depending on the pretreatment conditions and the composition of the feedstock, acetic acid levels in the feed stream to fermentation can range from about 0.1 to about 1.2 wt %, which is between about 6 and about 70 times more concentrated than the corn ethanol process and above known inhibition levels. Cellulosic ethanol conversion processes are also susceptible to contamination, which can add more acetic acid.

Thus, according to embodiments of the invention, the stream subjected to the step of fermenting contains about 0.1 to about 1.2 wt % acetic acid (including acetate species), or any range therebetween. For example, the stream subjected to fermentation may contain up to about 0.1, 0.2, 0.3, 0.4, 0.5, 0.6, 0.7, 0.8, 0.9, 1.0, 1.1 or 1.2 wt % acetic acid.

The inhibitory compounds set forth above are representative of the compounds present in a process stream produced from a lignocellulosic feedstock. It will be appreciated that the inhibitory compounds present depend on both the raw material and the pretreatment that is employed.

Process Streams Fed to the Treatment Process

The process stream(s) selected for further treatment in the treatment process, described in more detail below, and subsequent recycle, may contain reduced levels of inhibitors and/or other undesirable components relative to other streams generated in the process. Examples of such streams are provided in FIG. 1.

As shown in FIG. 1, the one or more process streams 2 for treatment may be obtained from a cellulosic conversion process 1, associated utilities 3 and/or from seal water 4. Process streams 2 obtained from the cellulosic conversion process 1 include spent cleaning solution, condensate streams and rectifier effluent. Those streams obtained from the associated utilities, such as a boiler or cooling tower, may include blowdowns and regenerated streams. Spent seal water can also be obtained from seal water 4. Each of these process streams are described in turn below.

A. Spent Cleaning Solution

Process equipment utilized during the cellulosic conversion process may be prone to scale or solids build-ups during operation of the cellulosic conversion process. A cleaning regime utilizing an appropriate cleaning solution may be employed to remove such build-ups and the resultant spent cleaning solution can be treated and re-circulated in the process. Pretreatment, hydrolysis, enzyme or ethanol fermentation and distillation equipment and solid-liquid separators are examples of process equipment that may require treatment with a cleaning solution. Furthermore, a cleaning solution may be utilized to sanitize process equipment, for example during fermentation, as discussed below.

As used herein, the term "spent cleaning solution" refers to any solution previously used to clean one or more pieces of process equipment in the cellulosic conversion process. The term includes any suitable solution used to clean process equipment for the purpose of scale removal, debris removal, disinfection, decontamination, or any other purpose as required. This includes alkali or acidic solutions. Spent cleaning solution may be generated in several of the processing steps in the production of ethanol or other fermentation products from cellulose, including but not limited to pretreatment, hydrolysis, enzyme or ethanol fermentation, distillation, filtration and evaporation.

In one embodiment of the invention, the solids or scale can be removed by cleaning with one or more cleaning solutions comprising either alkali or acid at elevated temperatures. In one embodiment the temperature is between about 50° C. and about 250° C., or between about 60° C. and about 220° C., or between about 60° C. and about 150° C., or between about 60° C. and about 95° C., or any temperature range therebetween. The temperature and chemical make-up of the cleaning solution will vary depending on the scale that is being treated.

Non-limiting examples of alkali that may be used in the practice of the invention include those selected from the group consisting of sodium hydroxide, potassium hydroxide, ammonia, ammonium hydroxide, potassium carbonate, potassium bicarbonate, sodium carbonate and sodium bicarbonate. In one embodiment of the invention, the alkali is sodium hydroxide or potassium hydroxide. In yet another embodiment of the invention, the alkali is sodium hydroxide.

Non-limiting examples of acid that may be used in the practice of the invention include those selected from the group consisting of phosphoric acid, sulfuric acid, hydrochloric acid, nitric acid and sulfurous acid. In one embodiment of the invention, the acid is phosphoric acid or sulfuric acid. In yet another embodiment of the invention the acid is phosphoric acid.

During fermentation, washing solutions can be employed to disinfect surfaces that are prone to contamination by microorganisms. Such solutions can be alkali or acidic, depending on the purpose of the treatment.

An example of scale that can build up in process equipment is lignin scale. The formation of lignin scale deposit and treatment methods to remove it, are described in co-owned WO 2011/094859, which is hereby incorporated by reference.

During or after the pretreatment process, any equipment that is exposed to feedstock undergoing a change in physical properties may be prone to scale deposit comprising lignin. The change in physical properties may include, but is not limited to, a change in temperature, pH, concentration, pressure or physical state. Examples of process equipment that may be prone to scale deposit comprising lignin include, but are not limited to, pumps; pipes; heat exchangers; in-line or other mixing equipment, including steam mixers; valves; agitators; scrapers; vessels and vessel internals, including but not limited to baffles, ports, impellors, spargers, and sampling devices; filtration units, including but not limited to pressure filters, microfilters, ultrafilters, nanofilters and reverse osmosis units; and conveyors.

Lignin scale can generally be removed with an alkali solution at elevated temperatures. The concentration of the alkali may be between about 0.5 wt % and about 10 wt %, or between about 0.5 and about 6 wt %, or between about 1 and about 5 wt %. The temperature required to remove the scale may be between about 50 and about 150° C., or between about 65° C. and about 120° C., or between about 75° C. and about 120° C. Higher temperatures can be utilized as well, including between about 120° C. and about 250° C.

In addition to lignin scale, fermentation equipment is prone to other types of scale formation. This scale can include but is not limited to the build-up of microbial cells, including yeast, fungus or bacterial biomass, biofilms, protein scale, inorganic scale and organic scale formation. In addition to treatment with alkali at elevated temperatures for lignin removal, these scales can be removed with acid at elevated temperatures. The concentration of the acid may be between about 0.5 wt % and about 5 wt %, or between about 1 and about 5 wt %. The temperature required to remove the scale may be between about 50 and about 150° C., or between about 65° C. and about 120° C., or between about 75° C. and about 95° C.

B. Process Condensate Streams

In one embodiment of the invention, the process stream selected for treatment prior to re-circulation is a process condensate stream obtained from a vapour stream that is subsequently condensed. The vapour stream may be obtained from a thermodynamic separation process, for example from a stream that has been subjected to a change in pressure, such as a drop in pressure, or for example by heating a stream.

Thermodynamic separation processes include those that separate streams based upon differences in their boiling points and include, but are not limited to, flash cooling, distillation and evaporation. The distillation may be an ethanol distillation process, as described previously, in which case the condensate stream is derived from an overhead stream.

In a further embodiment of the invention, the process condensate stream is an evaporator condensate resulting from a step of evaporating still bottoms in an evaporator unit and condensing vapour formed in the unit, as described previously. The still bottoms are concentrated and the vapour stream is then condensed by cooling. The evaporator condensate is then sent to the treatment process described herein.

Table 1 below provides the organic and inorganic content of still bottoms streams and condensates from a typical cellulosic conversion process. As can be seen from the table, condensates contain significantly lower levels of organic and inorganic compounds than still bottoms.

TABLE 1

Comparison of composition of still bottoms and condensate streams in a typical cellulosic conversion process

| Compounds | Typical still bottoms concentration for a cellulosic ethanol process (wt %) | Typical condensates concentration for a cellulosic ethanol process (wt %) |
| --- | --- | --- |
| Total organic compounds | 1-8% | 0-3% |
| Total inorganic compounds | 1-6% | 0-1% |

The concentration of acetic acid (measured as total acetic acid and acetate species) in the condensate may be between 0 to about 1.5 wt %. The pH of the still bottoms may be adjusted to influence the concentration of acetic acid in the evaporator condensate. During evaporation, some fraction of acetic acid will volatilize, while its conjugate base, acetate, will remain in solution and will not volatilize. The pKa of acetic acid is 4.75, which means that at this pH, 50% of the acetic acid in solution will be in the acid form, and 50% will be in the acetate form.

As the pH is increased above 4.75, the fraction of acetic acid that is present in the acetate form will increase, thereby reducing the fraction that is acetic acid and consequently the amount of acetic acid that is present in the evaporator condensate. A typical still bottoms stream has an acetic acid concentration of about 0.2 to about 1.2 wt %, while the condensate stream from an evaporation operated at increased pH will have an acetic acid concentration of only 0 to about 0.8 wt %. Thus, operating the evaporation at a pH at which all or a large proportion of the acetic acid is in the acetate form and sending the evaporator condensate to the treatment process may be desirable to reduce the organic load to the treatment process, thus reducing its capital and operating costs. According to such embodiments, the acetic acid (measured as total acetate and acetic acid species) in the process condensate stream may be less than about 0.8, 0.7, 0.6, 0.5, 0.4 or 0.3 wt %.

Conversely, it may also be desirable to lower the pH of the still bottoms to increase the fraction that is present as acetic acid, thereby increasing the concentration of acetic acid in the evaporator condensates. The condensate stream contains fewer chemical species than the still bottoms thereby making acetic acid recovery more feasible, if recovery of acetic acid is desirable. Increasing acetic acid in the condensate stream may also be desirable for reducing the acetic acid concentration in the still bottoms, if acetic acid interferes with the downstream processing of this stream. According to such embodiments of the invention, the acetic acid (measured as total acetate and acetic acid species) in the process condensate stream may be between about 0.8 wt % and about 1.5 wt %, between about 1.0 and about 1.3 wt % or any range therebetween.

In a further embodiment of the invention, the condensate stream is a flash cooling condensate resulting from a step of cooling a pretreated process stream in a flash tank, collecting the flashed stream and indirectly contacting it with other process streams to produce preheated process streams and condensed flash condensate. The flash condensate will also contain levels of acetic acid. Similar to the evaporator condensates, the concentrations of acetic acid in the flash condensates can vary depending on the composition in the feedstock, the pH of the process stream and the temperature of the flashing. For an acidic pretreatment process of lignocellulosic feedstock, acetic acid (measured as total acetate and acetic acid species) in the flash condensates can range from about 0.4 wt % to about 1.0 wt %, or from about 0.5 to about 0.8 wt %.

In some embodiments of the invention, different process condensate streams arising from the conversion process are combined and then subjected to the treatment process of the present invention.

The condensate stream may be further treated prior to anaerobic or aerobic treatment by a physical separation, such as reverse osmosis or filtration, described in more detail hereinafter.

C. Rectifier Effluent

As discussed above, the distillation unit may contain one or more separate beer and rectifying columns, in which case dilute beer is sent to the beer column where it is partially concentrated. From the beer column, the vapour goes to a rectification column for further purification.

Effluent from the rectifier may be sent to the treatment process. As used herein, the term "rectifier effluent" refers to any stream obtained from the bottom of a rectification column.

D. Blowdown Streams

Several utilities which support the production of ethanol or other fermentation products from a lignocellulosic feedstock generate blowdown streams. As used herein, a "blowdown stream" is a stream purged to maintain a suitable composition of a larger stream.

A blowdown stream typically arises from a cooling tower or a boiler. For example, a cooling tower generates a blowdown stream in order to maintain the amount of dissolved solids and other impurities at an acceptable level, to avoid scale and corrosion within the cooling tower system. As another example, a boiler generates a blowdown stream to maintain water parameters within prescribed limits to minimize scale, corrosion, carry-over, and other specific problems as well as maintain a low level of suspended solids within the system.

E. Regenerated Streams

As used herein, the "regenerated stream" refers to any stream resulting from regenerating a membrane or a resin used in a separation process. The separation process may include but is not limited to an ion exchange process or a reverse osmosis process.

In one embodiment of the invention the regenerated stream sent to the treatment process is a waste stream from a water treatment process. This may include, but is not limited to, the waste stream from a reverse osmosis unit used to purify fresh water, a waste stream from a water softener, used to soften water, or any other waste stream from a process to purify water.

F. Spent Seal Water

Many pieces of equipment used in the cellulosic conversion process contain mechanical seals. These devices form a seal between rotating surfaces, and may be included in any equipment with rotating parts, including, but not limited to, pumps, agitators, screw presses, compressors and mixers. Seal water is used to describe water that is sent to a sealing system, such as water used to cool the seal or to displace product that may have poor properties for use in a mechanical seal.

As used herein, "seal water" refers to any water that enters and then exits a mechanical seal that is contacted with water. For example, seal water may arise from a flushing operation utilized so as to ensure proper functioning of the mechanical seal.

Seal water should generally be clean water to avoid damage to the internal components of the mechanical seal, including abrasion, erosion, corrosion, or any other form of damage to the mechanical seal. Water introduced as seal water generally leaks externally to the seal, although internal leaking seals are also possible. If the mechanical seal is functioning properly, then there will be negligible leakage of contaminating components into the seal water flow, and the externally leaking seal water flow will consist of clean water. However, if the mechanical seal is not functioning properly, it is possible for internal process fluid to leak into the seal water, and subsequently leak externally to the equipment, and would require treatment before discharge or reuse in the process.

The number of pieces of equipment requiring seal water can, in many instances, be significant, resulting in a high demand for clean water to be used as seal water, and consequently a large volume of used seal water which requires treatment. Additionally, as equipment sizes increase, the amount of seal water required per piece of equipment also increases, which exacerbates the overall demand for seal water, and the subsequent treatment requirements.

Composition of Process Streams Selected for Treatment

One or more of the process streams selected for treatment may contain an organic content of less than about 5 wt % and/or an inorganic content of less than about 5 wt %.

For example, the organic content may be less than about 5.0, 4.5, 4.0, 3.5, 3.0, 2.5, 2.0, 1.5, 1.0 or 0.5 wt %. In further embodiments of the invention, the organic content is about 0.01 to about 5 wt %, or about 0.01 to about 4.0 wt %, about 0.01 to about 3.0 wt %, or about 0.01 to about 2.5 wt % or about 0.01 to about 2.0 wt %.

In some embodiments of the invention, the inorganic content is less than about 5.0, 4.5, 4.0, 3.5, 3.0, 2.5, 2.0, 1.5, 1.0 or 0.5 wt %. In further embodiments of the invention, the inorganic content is about 0.01 to about 5 wt %, or about 0.01 to about 4.0 wt %, about 0.01 to about 3.0 wt %, or about 0.01 to about 2.5 wt % or about 0.01 to about 2.0 wt %.

Organic compounds that may be present in the process streams include organic acids, including, but not limited to, furfural and acetic acid. Examples of inorganic compounds that may be present in the process streams include calcium, magnesium and sodium salts.

Treatment Process to Obtain a Treated Water Stream for Re-circulation

One or more of the foregoing process streams are (A-F) then subjected to a treatment process. The treatment process produces a treated water stream that can be re-circulated to the cellulosic conversion process or associated utilities.

Many different configurations and treatment options are encompassed by the present invention. Exemplary configurations for the treatment process are provided in FIGS. 2, 3A, 3B and 4, described in detail below. The treatment process of the invention comprises at least a step of feeding the one or more process streams to an anaerobic digester, an aerobic digester and/or a reverse osmosis unit. Each unit operation that may be employed in the treatment process is discussed in turn below.

Anaerobic Digestion

Anaerobic digestion involves the use of microorganisms to break down organic material for the purpose of waste management and energy production, to primarily produce methane and carbon dioxide. A mixed population of microbes is used to break down the organic material and may include, although is not limited to, acidogenic bacteria, acid-forming bacteria (acetogens), and methane-forming archaea (methanogens). Without being limiting, this consortium of microorganisms typically process incoming streams through a series of four general steps. These steps include hydrolysis, a chemical reaction where particulates are solubilized and large polymers converted into simpler monomers; acidogenesis, biological reaction where simple monomers are converted into volatile fatty acids; acetogenesis, a biological reaction where volatile fatty acids are converted into acetic acid, carbon dioxide, and hydrogen; and methanogenesis, a biological reaction where acetates are converted into methane and carbon dioxide, while hydrogen is consumed.

Anaerobic digesters may be designed and/or operated in a number of configurations including batch or continuous, mesophilic or thermophilic temperature ranges, and low, medium or high rate units. The rate refers to the chemical oxygen demand (COD) feed rate to the unit, high or low solids content and single or multistage. The choice of configuration will depend on a number of factors. These may include consideration of the nature of the feedstock to be treated, the level of treatment desired and/or required, capital, operating and maintenance cost considerations, including consideration of the equipment footprint. Other factors that may be considered in the configuration choice include operating parameters, including, but not limited to, residence time, temperature, pH and the nutrients supplied to the system.

One of the main products of anaerobic digestion is biogas which is produced during the final stage of the digestion process, methanogenesis. Biogas contains methane, which can be combusted to produce both heat and electricity. Excess electricity can be sold to suppliers or to the local grid.

Aerobic Digestion

Depending on the quality of the effluent from the anaerobic digester, it may be suitable for recycle into selected areas of the cellulosic conversion process, associated utilities and/or seal water system. However, the effluent stream may also require further treatment to be suitable for recycle. One possibility for additional treatment is aerobic digestion.

Aerobic digestion uses air and a consortium of microorganisms, also referred to as activated sludge, to reduce biological oxygen demand (BOD) and/or chemical oxygen demand (COD) in a process stream and produces treated water and carbon dioxide. Typically, an aerobic digestion system will include means to separate the treated water from the microbial consortium.

Aerobic digestion systems may be designed and/or operated using any suitable configuration known to those of skill in the art. Conventional processes typically include at least one aeration tank and at least one settling tank. There are many possible configurations for activated sludge processing, including the vessel size, configuration and numbers of vessels, continuous or batch operating modes, the aeration delivery method and rate, and the settling and separation method(s) to be used in the process. In practice, the selected configuration will depend on a numbers of factors. These may include the nature of the feedstock to be treated, the level of treatment desired and/or required, capital, operating and maintenance cost considerations, including consideration of the equipment footprint. Other factors that may be considered in the configuration choice include operating parameters, including residence time, aeration rate, temperature, pH and nutrients supplied to the system.

In addition to the conventional configurations, advances in the treatment of industrial effluents have led to the development of improved processes, such as the membrane bioreactor (MBR). The MBR, which can be used anaerobic or aerobic configuration, combines a bioreactor with a microbial consortium to break down components in the incoming process streams with a membrane process such as microfiltration or ultrafiltration. The membranes are submerged in the bioreactor, thereby replacing the settling tank or similar process in the conventional activated sludge processes. This configuration provides many benefits including eliminating the separate separation equipment and reducing equipment footprint, removing dependence upon settleability characteristics of the sludge, and allowing operation at higher sludge concentrations which reduces the volume of the aeration tank thereby further reducing the footprint required.

Physical Separation

Depending on the quality of the effluent stream from anaerobic or aerobic digestion, one or more of these streams may be suitable for recycle into the cellulosic conversion process, associated utilities or seal water system. However, the effluent streams from anaerobic or aerobic digestion may also require further treatment to be suitable for recycle into the cellulosic conversion process, the associated utilities and/or the seal water system. This further treatment may comprise any suitable physical separation process.

As used herein, a "physical separation" refers to any separation process in which at least two components are separated from one another by exploiting differences in their respective physical properties. Physical properties can include, but are not limited to, density, mass, solubility, particle size and distribution.

One example of a suitable physical separation is reverse osmosis. Reverse osmosis is a filtration method that removes many types of large molecules and ions from solutions by applying pressure to the solution when it is on one side of a selective membrane. The result is that the solute is retained on the pressurized side of the membrane and the pure solvent is allowed to pass to the other side. To be selective, this membrane does not allow large molecules or ions through the pores (holes), but allows smaller components of the solution (such as the solvent) to pass freely. Reverse osmosis involves a diffusive mechanism so that separation efficiency is dependent on solute concentration, pressure and water flux rate.

In addition to or instead of reverse osmosis, other types of physical separation can be used. Physical separation may be employed to remove larger debris or solids from a stream, or to remove very small particles or molecules from the stream. A variety of physical separation filtration equipment types are available, and the choice of technology will depend on a number of factors including, but not limited to, the identity and size of the material to be removed, the level of removal required, and capital, operating and maintenance cost considerations. Some of the types of physical separation technology that may be employed include, but are not limited to, filter presses, plate and frame presses, decanters, centrifuges, settling tanks, clarifiers, microfilters, ultrafilters, and nanofilters. One or more of these may be used to treat effluent from an anaerobic or an aerobic digestion process or a reverse osmosis system.

Chemical Treatments

In addition to, or instead of aerobic digestion or physical separation, chemical treatment methods can also be utilized to treat streams. As used herein, "chemical treatment" refers to any treatment that may be employed to alter or change the chemical composition of components of the stream. The chemical treatment can be a chemical separation technique, an example of which is a chemical separation by ion exchange. Ion exchange is a separation technique in which an ion from solution is exchanged for a similarly charged ion attached to an immobile solid particle. The ion exchange resins may be cation exchangers that have positively charged mobile ions available for exchange, or anion exchangers, whose exchangeable ions are negatively charged. The solid ion exchange particles may be either naturally occurring inorganic zeolites or synthetically produced organic resins.

Another example of a chemical separation technique is chemical precipitation. With chemical precipitation specific chemicals are added to react with species in solution to form new chemical compounds which are not soluble under the conditions of the precipitation. The new chemicals precipitate out of solution as solids, and can then be removed by standard physical separation techniques.

Other examples of chemical treatment methods may include but are not limited to ultraviolet light treatment or treatment with ozone.

Segregation of Streams for Treatment

In addition to selecting streams with lower levels of inhibitors for treatment and recycle, the invention involves the segregation of the selected streams for treatment according to the type and level of treatment required. By segregating the streams and subjecting them to the minimum level of treatment required to reduce inhibitor levels, such that the performance of the biocatalysts in the process are maintained, the overall capital and operating treatment costs can be reduced. By the term "segregation", it is meant to set apart or isolate certain process streams from others based on treatment requirements. The definition also includes combining certain streams based on their treatment requirements and segregating those combined streams.

Figure 2:
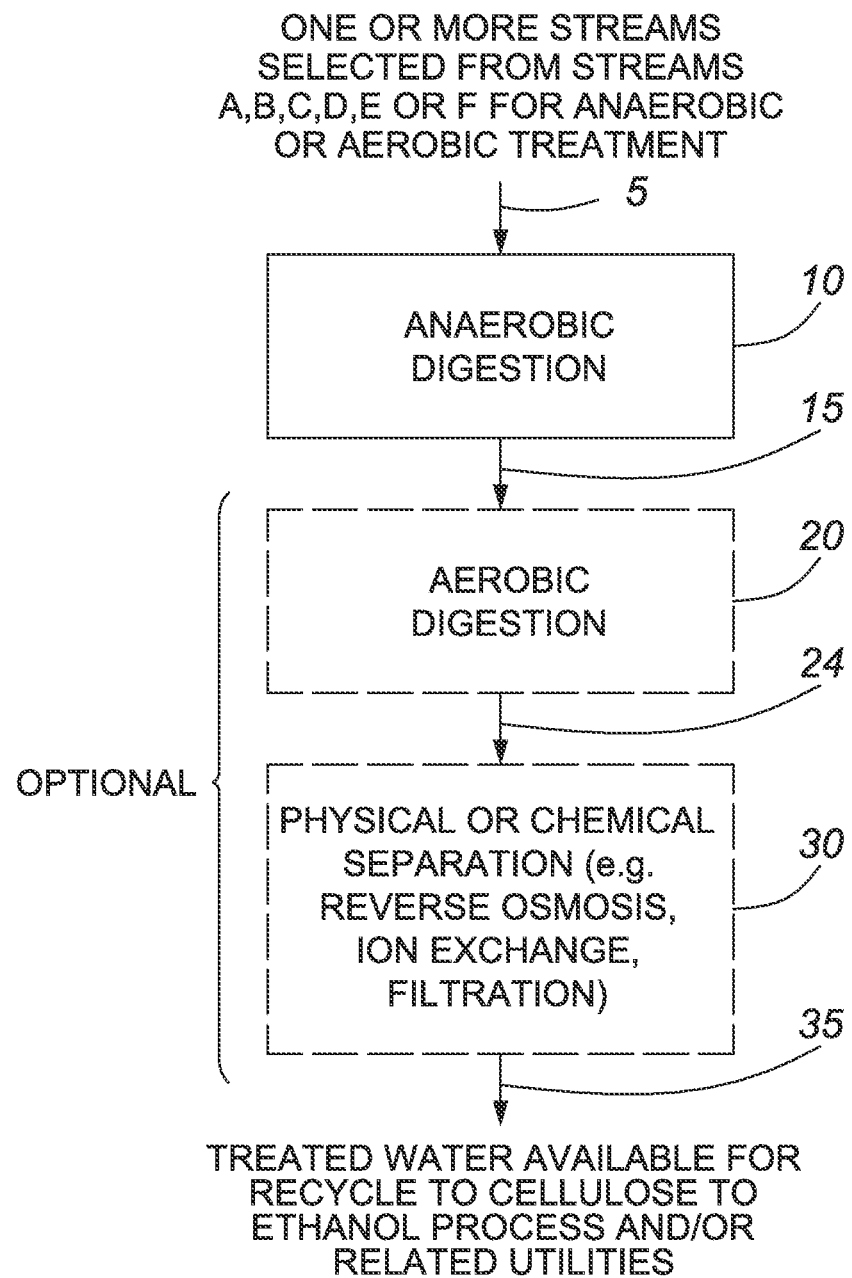
FIG. 2 depicts a treatment process in which process streams from a cellulosic conversion process, associated utilities and/or a seal water system are treated using anaerobic digestion, followed by optional steps of aerobic digestion and physical separation, to produce a treated water stream that is recycled.

Rather than segregating process streams, all of the streams can be combined and sent to anaerobic and then aerobic treatment (e.g., FIG. 2). Although this configuration will ensure sufficient treatment of the overall stream, the extent of treatment required and the size of the treatment equipment needed for the treatment can be cost prohibitive. Segregation of streams in accordance with the invention overcomes these limitations.

In some embodiments of the invention, it is advantageous to send those streams that require only anaerobic treatment to an anaerobic treatment system, and those streams that require only aerobic treatment to an aerobic treatment system. This minimizes the size of both treatment systems only to what is necessary to provide streams with suitable levels of inhibition for recycle.

In yet further embodiments of the invention, aerobic treatment may not be necessary. For example, process condensate streams will typically contain organic compounds, which can potentially be treated by anaerobic digestion or by aerobic digestion. Aerobic digestion provides a higher level of treatment but at a higher cost. For some condensate streams, anaerobic treatment will be sufficient to reduce the inhibition level, and in these cases it would be most advantageous to only treat with an anaerobic digester prior to recycle, and avoid the cost of aerobic treatment altogether. However, for other condensate streams, aerobic treatment may be required to sufficiently reduce the inhibitory compounds in the stream such that they are suitable for recycle.

It is also possible that effluent from an anaerobic digester, or a portion thereof, may be sent to an aerobic digester such that the combination of the effluent from the anaerobic and the aerobic digesters meets the overall quality requirements for recycle in the process.

In a process utilizing recycle, a purge from the system is typically required to ensure that components do not build up in the system over time with repeated recycle. Thus, it would be advantageous to segregate streams from others that have (i) high concentrations of inhibitory compounds; and/or (ii) require a higher level of treatment for recycle in the process than they would for discharge from the process. These streams could be treated for discharge, for example, in a secondary aerobic digester, and remain segregated from the other streams, thereby purging high concentrations of unwanted compounds from the process and minimizing the overall treatment costs.

Spent cleaning solutions may be advantageous to segregate for minimal treatment and discharge from the process as these streams will likely contain organic compounds as well as inorganic compounds and suspended solids. However, the composition of such solutions will depend on the equipment being cleaned and the type of build-up being removed.

In another example, blowdown streams, which typically result from a cooling tower or a boiler operation, will generally contain high levels of inorganic materials and, accordingly, would be most suitably treated with a reverse osmosis unit or a chemical separation process, such as ion exchange. It would therefore be advantageous to segregate these streams and send them only to a reverse osmosis or ion exchange treatment system for recycle in the process, minimizing the overall treatment system costs. Feeding this stream to anaerobic or aerobic digesters may not result in sufficient treatment for recycle in the process.

By collecting and segregating the streams according to their treatment requirements, the size of the individual treatment units, including anaerobic digestion, aerobic digestion, physical separation, including reverse osmosis, and chemical treatment, including ion exchange, can be minimized, thereby reducing the overall operating and capital costs of the treatment area as a whole.

Examples of treatment processes in which process streams are segregated according to their treatment requirements are provided in FIGS. 3A, 3B and 4 described below.

Re-circulation of Treated Water Streams

The treated water stream resulting from the treatment process is re-circulated or recycled into the cellulosic conversion process, associated utilities, seal water system or a combination thereof. The terms "re-circulating and recycling" are used interchangeably herein. It should be understood that more than one treated water stream may be re-circulated during the step of re-circulating.

The amount of the treated water stream recycled to the cellulosic conversion process, associated utilities or the seal water system may be about 30% to about 99%, or between about 60% and about 95%, or between about 70% and about 90%, or any range therebetween. It should be understood that some amount of purge will be required during recycle. The treated water stream may be fed to a storage tank that is topped up with fresh water as needed.

Examples of stages of the process in which the treated water stream can be re-circulated include, but are not limited to, one or more stages of the cellulosic conversion process, including: pretreatment, enzymatic hydrolysis, enzyme fermentation, filtration, ethanol fermentation, residue processing and a cleaning system, such as a clean in place (CIP) system The treated water stream can also be re-circulated to the associated utilities or a seal water system.

By the term "associated utilities", it is meant any equipment used to support the cellulosic conversion process. This may include a cooling tower, chiller, fresh water treatment system, fire water system, compressed air system, chemical storage systems and/or a boiler feed water system.

By the term "seal water system", it is meant any system that supplies water to mechanical seals. For example, seal water may be used in a flushing operation utilized so as to ensure proper functioning of the mechanical seal, as discussed above.

Detailed Description of the Preferred Embodiments

The process of the present invention will be described by reference to the figures. It should be understood, however, that the figures shown are merely exemplary of apparatus suitable for carrying out the present invention and other equivalent means may be utilized without departing from the spirit of the invention.

As set forth in FIG. 2, one or more process streams 5 are selected for treatment by a treatment process comprising at least a step of anaerobic digestion 10. The process stream 5 fed to anaerobic digestion comprises one or more streams labeled A, B, C, D, E or F in FIG. 1, namely spent cleaning solutions, condensate streams, rectifier effluent, blowdown streams, regenerated streams and spent seal water, respectively. Subsequent to anaerobic digestion 10, the effluent stream 15 from the anaerobic digestion 10 is optionally treated in aerobic digestion 20 and an effluent stream 24 from the aerobic digestion may be subjected to further physical or chemical separation 30, such as reverse osmosis, ion exchange or filtration. The treated water 35 resulting from the treatment process is then recycled to the cellulosic conversion process and/or related utilities. As noted, such a treatment process requires large equipment and high operating costs, which negatively impacts the economics of the process.

Figure 3A:
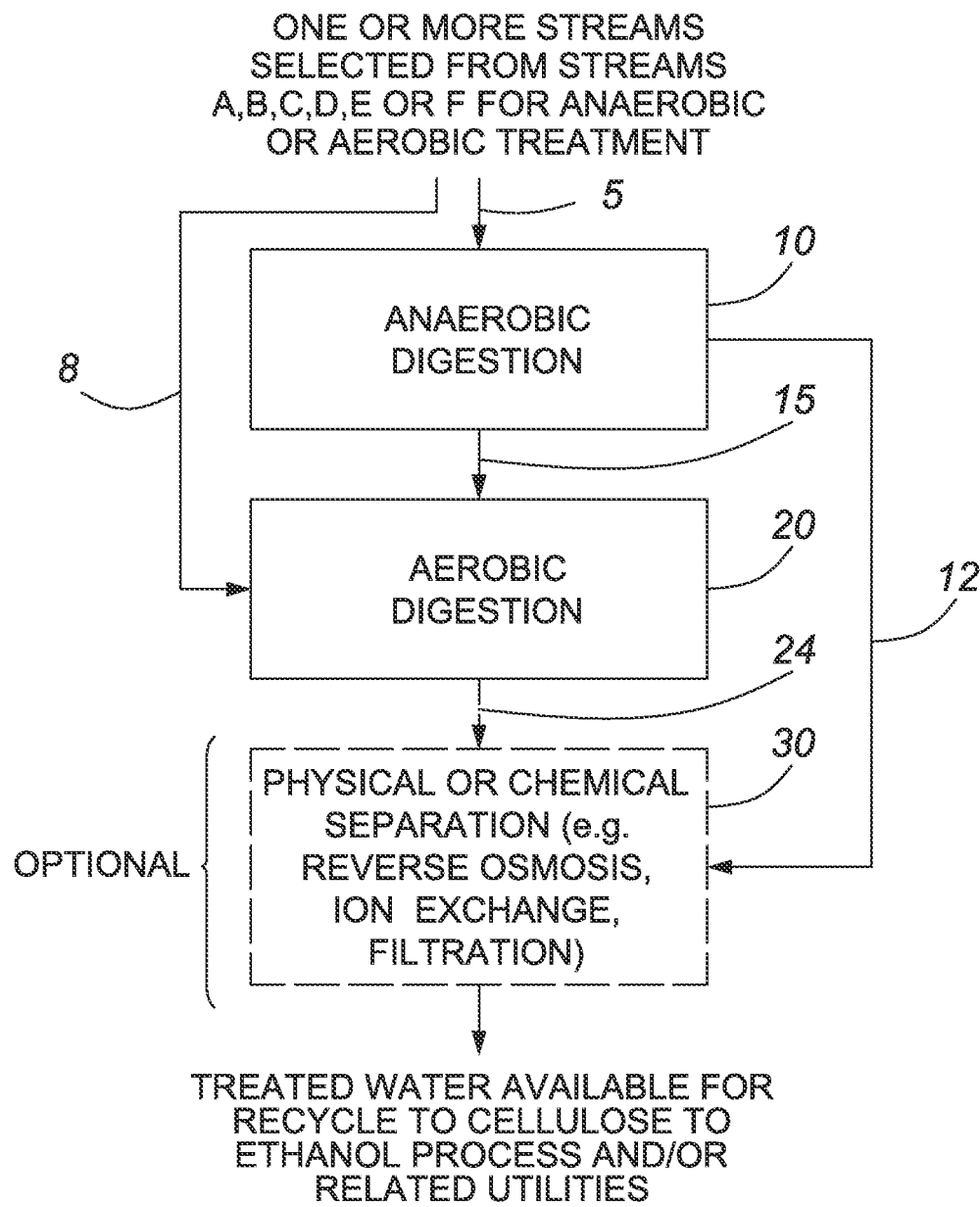
FIG. 3A depicts a treatment process in which some process streams from a cellulosic conversion process, associated utilities and/or a seal water system are treated using anaerobic digestion, while others are treated by aerobic digestion, followed by an optional step of physical separation, to produce a treated water stream that is recycled.

Referring to FIG. 3A, which describes an embodiment of the present invention, one or more streams 5 are fed to anaerobic digestion 10, while one or more other streams 8 are fed to aerobic digestion 20. Stream 8 sent to aerobic digestion 20 may include one or more of spent cleaning solutions, process condensate streams, rectifier effluent and spent seal water. However, it should be understood that the composition of stream 5 and 8 can vary. For example, both streams may contain process condensates, possibly containing different types of process condensates or a fractional amount of the same type of process condensate. An effluent stream 15 resulting from anaerobic digestion is treated in aerobic digestion 20 and, optionally, the effluent stream 24 from the aerobic digestion is subjected to a further physical or chemical separation 30, such as reverse osmosis, ion exchange or filtration. Furthermore, an effluent stream 12 from anaerobic digestion 10 may be sent directly to the optional physical or chemical separation 30. The treated water resulting from the treatment process is then recycled to the cellulosic conversion process and/or related utilities.

Figure 3B:
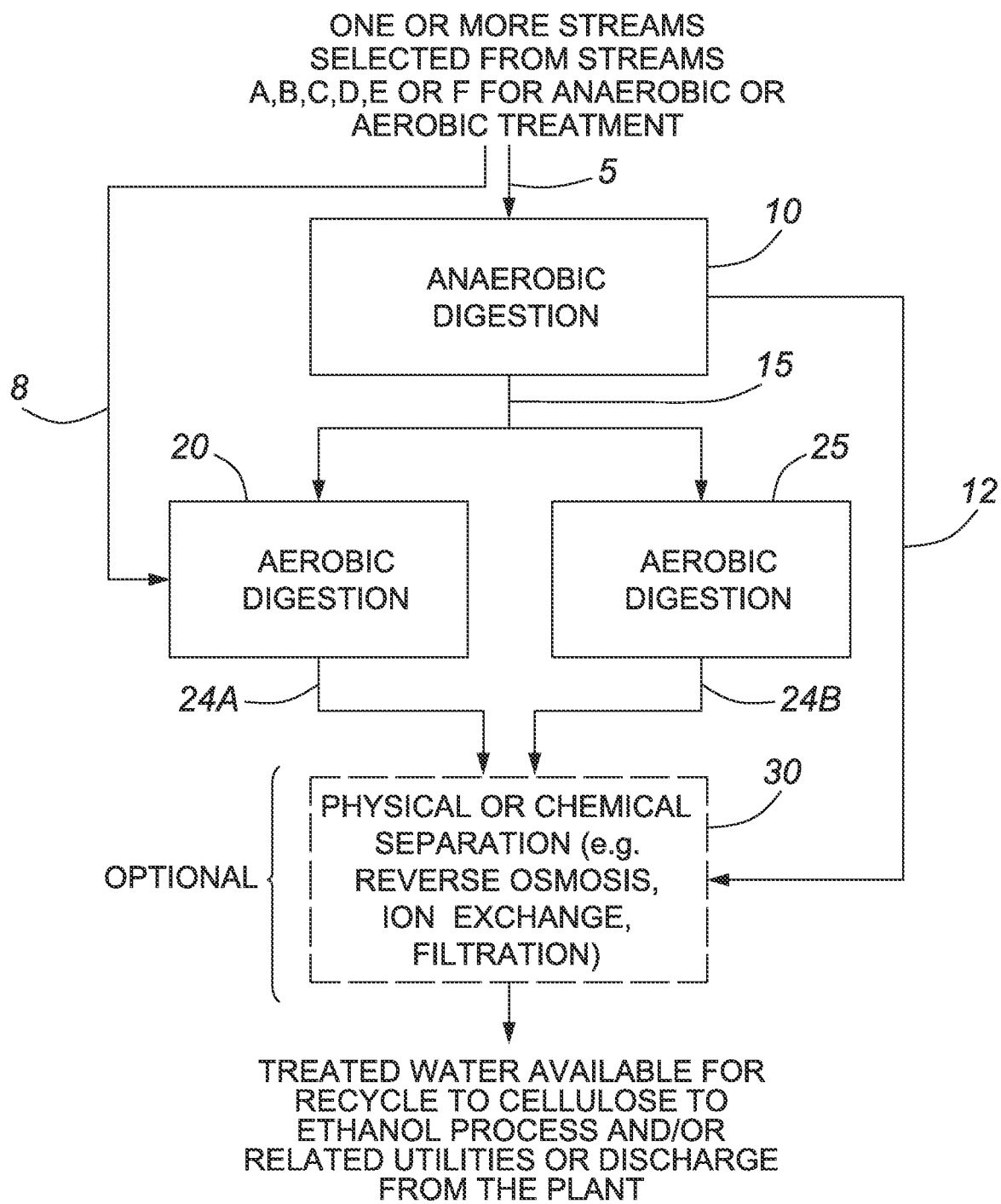
FIG. 3B is similar to FIG. 3A, except in FIG. 3A one aerobic digestion is employed, while in FIG. 3B, two aerobic digestion steps are employed.

FIG. 3B is identical to FIG. 3A except that an additional aerobic digester 25 is utilized in the configuration. Stream 15 is split into two streams, one of which is sent to aerobic digester 20 and the other to aerobic digester 25. Effluent streams 24A and 24B, from the aerobic digesters 20 and 25, respectively, are fed to the physical or chemical separation 30. Optionally, the effluent from one of the aerobic digesters 20 or 25 is discharged to the environment.

Figure 4:
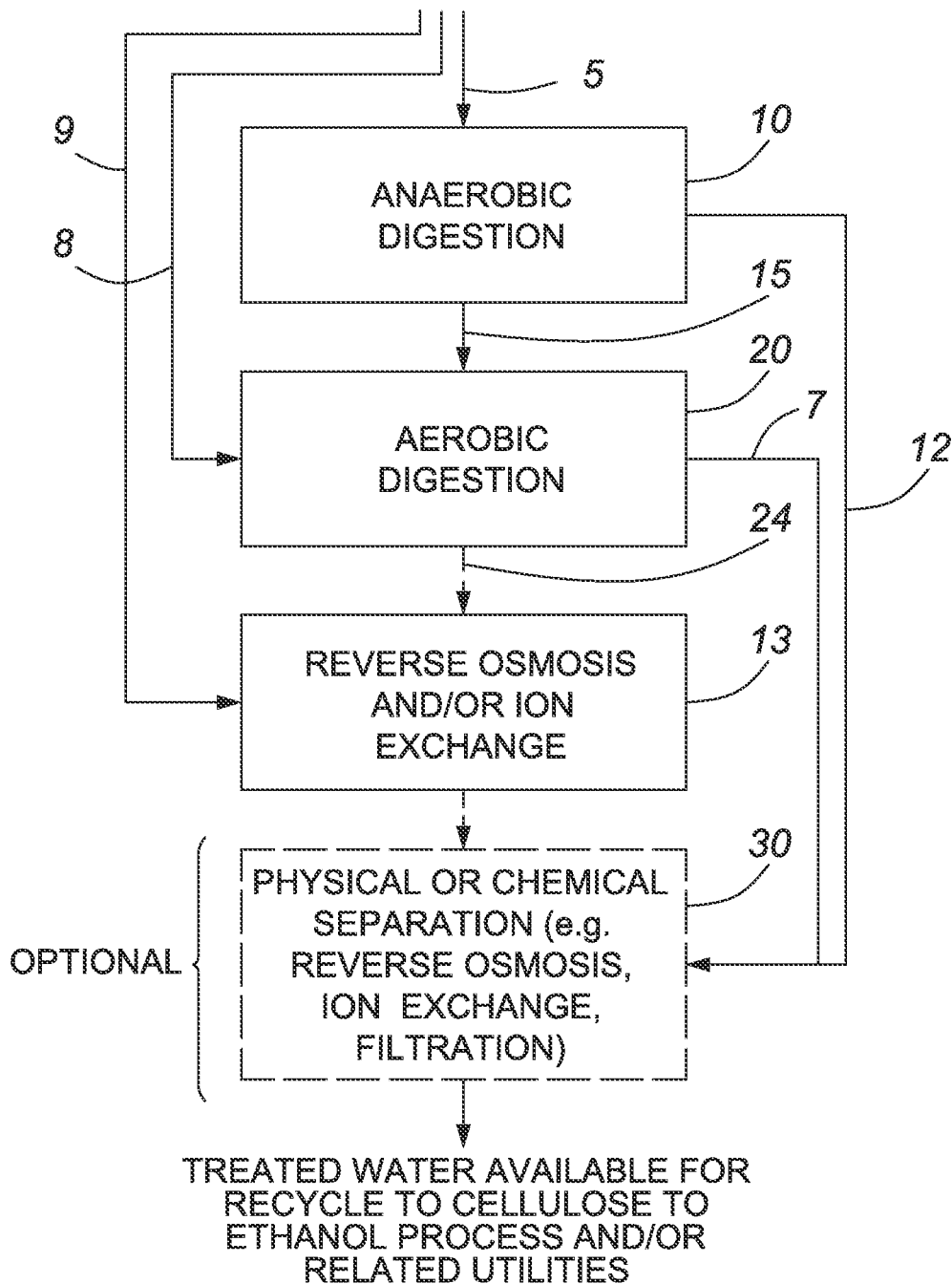
FIG. 4 depicts a treatment process in which some process streams from a cellulosic conversion process, associated utilities and/or a seal water system are treated using anaerobic digestion, others are treated by aerobic digestion, while others are treated using reverse osmosis, followed by an optional step of physical separation, to produce a treated water stream that is recycled.

Turning now to FIG. 4, one or more streams 5 are fed to anaerobic digestion 10, while others streams 8 are fed to aerobic digestion 20, and others 9 to reverse osmosis or ion exchange 13. Streams 9 sent to reverse osmosis or ion exchange may contain or more of the blowdown, regeneration or spent seal water streams. The composition of streams 5 and 8 may vary as required. An effluent stream 15 resulting from anaerobic digestion is treated in aerobic digestion 20 and the effluent stream 24 from the aerobic digestion is subjected to reverse osmosis and/or ion exchange 13. Furthermore, an effluent stream 12 from anaerobic digestion 10 may be sent directly to the optional physical or chemical separation 30. Similarly, an effluent stream 7 from anaerobic digestion 20 may be sent to optional physical or chemical separation 30. The treated water resulting from the treatment process is then recycled to the cellulosic conversion process and/or related utilities.

The invention claimed is:

1. A cellulosic conversion process employing water recycle, the process comprising the steps of:
   (i) pretreating a lignocellulosic feedstock to produce a pretreated feedstock;
   (ii) hydrolyzing cellulose in the pretreated feedstock with cellulase enzymes to produce glucose;
   (iii) fermenting at least the glucose with microorganisms to produce a fermentation broth comprising alcohol;
   (iv) distilling the fermentation broth to produce concentrated alcohol and still bottoms;
   (v) obtaining at least two of the following process streams from the cellulosic conversion process, associated utilities, or seal water system:
      (a) spent cleaning solution used to clean process equipment utilized during any of the preceding steps (i) to (iv);
      (b) a process condensate stream obtained during said cellulosic conversion process;
      (c) a rectifier effluent stream obtained from the step of distilling the fermentation broth;
      (d) a blowdown stream obtained from a cooling tower or boiler system;
      (e) a regenerated stream; and
      (f) spent seal water obtained from one or more pieces of equipment used during any of the preceding steps (i) to (iv);
   (vi) conducting a treatment process comprising subjecting one or more of said at least two process streams to a first treatment comprising an anaerobic digestion and subjecting one or more other streams of said at least two process streams to a second treatment comprising an aerobic digestion, said treatment process resulting in one or more treated water streams,
      wherein said first treatment and said second treatment are different,
      wherein said one or more streams subjected to the first treatment and said one or more other streams subject to the second treatment are segregated according to treatment requirements,
      wherein said one or more other streams subjected to said second treatment is selected from (a), (b), (c), and (f), and
      wherein said second treatment comprises bypassing anaerobic digestion; and
   (vii) re-circulating the one or more treated water streams resulting from the treatment process to the cellulosic conversion process, associated utilities, seal water system or a combination thereof.

2. The process of claim 1, wherein said one or more treated water streams that are re-circulated comprise either an effluent stream from the anaerobic digestion, an effluent stream from aerobic digestion, both effluent streams, or one or more streams derived therefrom.

3. The process of claim 1, further comprising feeding an effluent stream from the anaerobic digestion to the aerobic digestion.

4. The process of claim 3, further comprising obtaining a second effluent stream from the anaerobic digestion and feeding said second effluent stream to a physical separation, a chemical separation or discharging said second effluent stream from the process.

5. The process of claim 3, wherein the one or more treated water streams that are re-circulated comprise an effluent stream from the aerobic digestion, or one or more streams derived therefrom, and
   wherein the treatment process further comprises the use of a second aerobic digestion, wherein an effluent stream from said second aerobic digestion, or one or more streams derived therefrom, is discharged from the process.

6. The process of claim 2, wherein the effluent stream from the anaerobic or aerobic digestion, or both effluent streams, are further treated by one or more of reverse osmosis, ion exchange and filtration to remove sediment, ions or both sediment and ions prior to the step of re-circulating.

7. The process of claim 1, wherein the treatment process further comprises subjecting the blowdown stream, the regenerated stream, the spent seal water stream, or a combination thereof, to a reverse osmosis or ion exchange operation.

8. The process of claim 1, wherein the two or more process streams obtained from step (v) comprise at least the process condensate stream.

9. The process of claim 1, wherein the treatment process reduces the concentration of acetic acid.

10. The process of claim 1, wherein step (v) comprises combining two or more of the process streams.

11. The process of claim 1, wherein the condensate stream is a flash condensate stream resulting from a step of flashing conducted on the pretreated feedstock to reduce the temperature of same.

12. The process of claim 1, wherein the condensate stream is an evaporator condensate stream resulting from a step of evaporating the still bottoms in an evaporator unit and condensing vapor obtained therefrom.

13. The process of claim 1, wherein the one or more treated water streams are re-circulated to the step of pretreating, hydrolyzing, fermenting, a cleaning system, a residue processing stage, or a combination thereof.

14. The process of claim 1, wherein the one or more treated water streams are re-circulated to the cooling tower system, boiler feed water system, or any combination thereof.

15. A process for recycling water in a cellulosic conversion process that produces an alcohol, the process comprising the steps of:
   (i) pretreating a lignocellulosic feedstock to produce a pretreated lignocellulosic feedstock;
   (ii) hydrolyzing cellulose in the pretreated feedstock with cellulase enzymes to produce glucose;
   (iii) fermenting at least the glucose with microorganisms to produce a fermentation broth comprising the alcohol;
   (iv) distilling the fermentation broth to produce concentrated alcohol and still bottoms;
   (v) obtaining at least two process streams for further treatment and recycle, wherein the at least two process streams arise from the cellulosic conversion process, associated utilities, or a seal water system, said at least two process streams selected from:
      (a) spent cleaning solution used to clean process equipment utilized during any of the preceding steps (i) to (iv);
      (b) a process condensate stream obtained during said cellulosic conversion process;
      (c) a rectifier effluent stream obtained from the step of distilling the fermentation broth;

(d) a blowdown stream obtained from a cooling tower or boiler system;
(e) a regenerated stream; and
(f) spent seal water obtained from one or more pieces of equipment used during any of the preceding steps (i) to (iv);

(vi) subjecting said at least two process streams to a treatment process, thereby producing one or more treated water streams, said treatment process comprising:

segregating said at least two process streams according to treatment requirements, subjecting one or more of the segregated streams to a first treatment comprising anaerobic digestion, and subjecting one or more of the segregated streams to a second treatment comprising aerobic digestion, wherein said one or more of the segregated streams subjected to said second treatment is selected from (a), (b), (c), and (f), and wherein said second treatment comprises bypassing anaerobic digestion; and (vii) re-circulating the one or more treated water streams to the cellulosic conversion process, associated utilities, seal water system or a combination thereof.

16. The process of claim 15, wherein one of said process streams is discharged to the environment.

17. The process of claim 15, wherein one or more of the process streams are subjected to reverse osmosis, ion exchange or a combination thereof.

18. The process of claim 15, wherein the one or more process streams subjected to the second treatment includes a process stream from at least one of the spent cleaning solution, the process condensate stream, the rectifier effluent or the spent seal water.

19. The process of claim 15, wherein the one or more process streams sent to the first and second treatments each result from combining two or more of the process streams of step (v).

20. A process for recycling water in a cellulosic conversion process that produces a fermentation product, the process comprising the steps of:

(i) obtaining process streams for further treatment and recycle, wherein the process streams arise from the cellulosic conversion process, associated utilities or a seal water system;

(ii) subjecting said process streams to a treatment process, thereby producing one or more treated water streams, said treatment process comprising:

segregating said process streams according to treatment requirements and feeding two or more of the segregated streams to respective separate treatments, wherein said respective separate treatments include a first treatment comprising anaerobic digestion, and a second treatment comprising aerobic digestion, wherein the segregated streams fed to the second treatment are selected from spent cleaning solution used to clean process equipment, a process condensate stream obtained during said cellulosic conversion process, a rectifier effluent stream, or spent seal water, wherein said second treatment comprises bypassing anaerobic digestion, and wherein each of the process streams comprises less than 5 wt % organic content and less than 5 wt % inorganic content; and (iii) re-circulating the one or more treated water streams to the cellulosic conversion process, associated utilities, seal water system or a combination thereof.

21. The process of claim 20, comprising discharging a treated stream from the second treatment without recycle.

* * * * *